(12) United States Patent
Weaver et al.

(10) Patent No.: US 8,663,463 B2
(45) Date of Patent: Mar. 4, 2014

(54) EXTRACORPOREAL FLUID CIRCUIT AND RELATED COMPONENTS

(75) Inventors: Colin Weaver, Pleasanton, CA (US); Martin Joseph Crnkovich, Walnut Creek, CA (US); Michael Emmanuel Kotsos, Walnut Creek, CA (US); John Marion Frazer, Concord, CA (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 857 days.

(21) Appl. No.: 12/388,003

(22) Filed: Feb. 18, 2009

(65) Prior Publication Data

US 2010/0206784 A1 Aug. 19, 2010

(51) Int. Cl.
*B01D 11/00* (2006.01)
*B01D 35/00* (2006.01)

(52) U.S. Cl.
USPC ............. 210/94; 210/640; 210/641; 210/767; 210/120; 210/321.84; 210/436; 210/472; 210/506

(58) Field of Classification Search
None
See application file for complete search history.

(56) References Cited

U.S. PATENT DOCUMENTS

| | | | |
|---|---|---|---|
| 3,946,731 A | 3/1976 | Lichtenstein | |
| 3,982,538 A | 9/1976 | Sharpe | |
| 3,985,135 A | 10/1976 | Carpenter et al. | |
| 3,996,027 A | 12/1976 | Schnell et al. | |
| 4,014,206 A | 3/1977 | Taylor | |
| 4,026,669 A | 5/1977 | Leonard et al. | |
| 4,061,031 A | 12/1977 | Grimsrud | |
| 4,137,160 A | 1/1979 | Ebling et al. | |
| 4,187,057 A | 2/1980 | Xanthopoulos | |
| 4,231,370 A * | 11/1980 | Mroz et al. | 604/361 |
| 4,370,983 A | 2/1983 | Lichtenstein | |
| 4,459,139 A | 7/1984 | vonReis et al. | |
| 4,488,961 A | 12/1984 | Spencer | |
| 4,530,759 A | 7/1985 | Schal | |
| 4,572,724 A * | 2/1986 | Rosenberg et al. | 96/6 |
| 4,590,227 A | 5/1986 | Nakamura et al. | |
| 4,643,713 A | 2/1987 | Viitala | |
| 4,662,906 A | 5/1987 | Matkovich et al. | |
| 4,695,385 A | 9/1987 | Boag | |
| 4,702,675 A | 10/1987 | Aldrovandi et al. | |
| 4,702,829 A | 10/1987 | Polaschegg et al. | |
| 4,888,004 A | 12/1989 | Williamson | |
| 4,997,464 A | 3/1991 | Kopf | |

(Continued)

FOREIGN PATENT DOCUMENTS

| | | |
|---|---|---|
| DE | 102005001779 | 9/2006 |
| EP | 0 327 136 | 8/1989 |

(Continued)

OTHER PUBLICATIONS

Acu-men, Acute Dialysis Machine Operating Instructions, Software Version 1.0, Fresenius MY acu-men, 1/05.96 (OP), 146 pages.

(Continued)

*Primary Examiner* — Vickie Kim
*Assistant Examiner* — Allison Fitzsimmons
(74) *Attorney, Agent, or Firm* — Fish & Richardson P.C.

(57) ABSTRACT

A vent assembly is described for use in an extracorporeal fluid unit. A vent structure adjacent to a micro-porous membrane forms the assembly. The vent structure is porous and changes color when the vent structure becomes wet, thereby providing a visual indication that the vent structure has been exposed to liquid.

40 Claims, 22 Drawing Sheets

(56) References Cited

U.S. PATENT DOCUMENTS

| | | | |
|---|---|---|---|
| 5,061,236 A | 10/1991 | Sutherland et al. | |
| 5,330,425 A | 7/1994 | Utterberg | |
| 5,425,173 A | 6/1995 | Moss et al. | |
| 5,441,636 A | 8/1995 | Chevallet et al. | |
| 5,460,490 A | 10/1995 | Carr et al. | |
| 5,498,338 A | 3/1996 | Kruger et al. | |
| 5,540,265 A | 7/1996 | Polaschegg et al. | |
| 5,578,070 A | 11/1996 | Utterberg | |
| 5,591,344 A | 1/1997 | Kenley et al. | |
| 5,614,677 A | 3/1997 | Wamsiedler et al. | |
| 5,628,908 A | 5/1997 | Kamen et al. | |
| 5,643,205 A | 7/1997 | Utterberg | |
| 5,651,893 A | 7/1997 | Kenley et al. | |
| 5,674,390 A | 10/1997 | Matthews et al. | |
| 5,674,404 A | 10/1997 | Kenley et al. | |
| 5,690,831 A | 11/1997 | Kenley et al. | |
| 5,711,883 A | 1/1998 | Folden et al. | |
| 5,714,060 A | 2/1998 | Kenley et al. | |
| 5,725,776 A | 3/1998 | Kenley et al. | |
| 5,788,671 A | 8/1998 | Johnson | |
| 5,849,065 A | 12/1998 | Wojke | |
| 5,863,421 A | 1/1999 | Peter | |
| 5,928,177 A | 7/1999 | Brugger et al. | |
| 5,938,634 A | 8/1999 | Packard | |
| 5,989,423 A | 11/1999 | Kamen et al. | |
| 6,179,801 B1 | 1/2001 | Holmes et al. | |
| 6,196,987 B1 | 3/2001 | Holmes et al. | |
| 6,200,287 B1 | 3/2001 | Keller et al. | |
| 6,231,537 B1 | 5/2001 | Holmes et al. | |
| 6,234,989 B1 | 5/2001 | Brierton et al. | |
| 6,280,406 B1 | 8/2001 | Dolecek et al. | |
| 6,336,916 B1 | 1/2002 | Bormann et al. | |
| 6,337,049 B1 | 1/2002 | Tamari | |
| 6,361,518 B1 | 3/2002 | Brierton et al. | |
| 6,383,158 B1 | 5/2002 | Utterberg et al. | |
| 6,409,696 B1 | 6/2002 | Toavs et al. | |
| 6,497,674 B1 | 12/2002 | Steele et al. | |
| 6,497,676 B1 | 12/2002 | Childers et al. | |
| 6,514,225 B1 | 2/2003 | Utterberg et al. | |
| 6,536,278 B1 | 3/2003 | Scagliarini | |
| 6,695,803 B1 | 2/2004 | Robinson et al. | |
| 6,725,726 B1 | 4/2004 | Adolfs et al. | |
| 6,730,055 B2 | 5/2004 | Bainbridge et al. | |
| 6,743,201 B1 | 6/2004 | Dönig et al. | |
| 6,755,801 B2 | 6/2004 | Utterberg et al. | |
| 6,764,460 B2 | 7/2004 | Dolecek et al. | |
| 6,790,195 B2 | 9/2004 | Steele et al. | |
| 6,852,090 B2 | 2/2005 | Burbank et al. | |
| 6,887,214 B1 | 5/2005 | Levin et al. | |
| 6,979,309 B2 | 12/2005 | Burbank et al. | |
| 7,021,148 B2 | 4/2006 | Kuhn et al. | |
| 7,115,107 B2 | 10/2006 | Delnevo et al. | |
| 7,238,164 B2 | 7/2007 | Childers et al. | |
| 7,476,209 B2 | 1/2009 | Gara et al. | |
| 7,517,387 B2 | 4/2009 | Chevallet et al. | |
| 7,603,907 B2 | 10/2009 | Reiter et al. | |
| 7,621,983 B2 | 11/2009 | Neri | 96/9 |
| 7,871,391 B2 | 1/2011 | Folden et al. | |
| 7,892,331 B2 | 2/2011 | Childers et al. | |
| 7,892,332 B2 | 2/2011 | Prisco et al. | |
| 7,905,853 B2 | 3/2011 | Chapman et al. | |
| 8,110,104 B2 | 2/2012 | Crnkovich et al. | |
| 2002/0014462 A1 | 2/2002 | Muller | |
| 2002/0072718 A1 | 6/2002 | Brugger et al. | |
| 2002/0179527 A1 | 12/2002 | Yao | |
| 2004/0019312 A1 | 1/2004 | Childers et al. | |
| 2004/0238416 A1 | 12/2004 | Burbank et al. | |
| 2005/0054968 A1 | 3/2005 | Giannella | |
| 2005/0126998 A1 | 6/2005 | Childers | |
| 2005/0131332 A1 | 6/2005 | Kelly et al. | |
| 2005/0132826 A1* | 6/2005 | Teugels | 73/866.5 |
| 2005/0230292 A1 | 10/2005 | Beden et al. | |
| 2007/0078369 A1 | 4/2007 | Tamari | |
| 2007/0086924 A1 | 4/2007 | Moses | |
| 2007/0106198 A1 | 5/2007 | Folden et al. | |
| 2007/0112297 A1 | 5/2007 | Plahey et al. | |
| 2007/0193940 A1 | 8/2007 | Duchamp et al. | |
| 2007/0269340 A1 | 11/2007 | Dannenmaier et al. | |
| 2008/0275364 A1* | 11/2008 | Conway et al. | 600/576 |
| 2009/0012449 A1 | 1/2009 | Lee et al. | |
| 2009/0071911 A1 | 3/2009 | Folden et al. | |
| 2009/0084721 A1 | 4/2009 | Yardimci et al. | |
| 2009/0101576 A1 | 4/2009 | Rohde et al. | |
| 2009/0216211 A1 | 8/2009 | Beden et al. | |
| 2009/0320684 A1 | 12/2009 | Weaver | |
| 2010/0133189 A1 | 6/2010 | Maierhofer et al. | |
| 2010/0206784 A1 | 8/2010 | Weaver et al. | |
| 2010/0222735 A1 | 9/2010 | Plahey et al. | |
| 2010/0292627 A1 | 11/2010 | Caleffi et al. | |
| 2011/0120946 A1 | 5/2011 | Levin et al. | |

FOREIGN PATENT DOCUMENTS

| | | |
|---|---|---|
| EP | 0458041 | 11/1991 |
| EP | 0 728 509 | 8/1996 |
| EP | 0887100 | 12/1998 |
| EP | 1 529 545 | 5/2005 |
| EP | 1 547 630 | 6/2005 |
| EP | 1 728 526 | 12/2006 |
| EP | 1 894 587 | 3/2008 |
| EP | 2 226 087 | 9/2010 |
| JP | 2003-180834 | 7/2003 |
| JP | 2005-530543 | 10/2005 |
| WO | 9640322 A | 12/1996 |
| WO | WO 0108722 | 2/2001 |
| WO | 01/50949 | 7/2001 |
| WO | WO 0164312 | 9/2001 |
| WO | WO 02/26286 | 4/2002 |
| WO | WO 2004/000391 | 12/2003 |
| WO | WO 2005/044340 | 5/2005 |
| WO | WO 2005/044341 | 5/2005 |
| WO | WO 2005/065745 | 7/2005 |
| WO | WO 2005077490 | 8/2005 |
| WO | 2007/050211 | 5/2007 |
| WO | 2008/002370 | 1/2008 |

OTHER PUBLICATIONS

Gambro®, "Prismaflex™, Anticipating Critical Care needs and taking our innovative response . . . to new heights", © 2004, Gambro Inc., Lakewood, CO, 8 pp.

Gambro®, "DEHP-Free Cartridge Blood Sets", © Nov. 2004, Gambro, Inc, Lakewood, CO, 4 pp.

Garnbro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.

Gambro®, "Prisma® HF 1000, For Increased Filtration Capacity", © Aug. 2001, Gambro Renal Products, Inc., Lakewood, CO, 2 pp.

Manns, Markus et al., "The acu-men: A new device for continuous renal replacement therapy in acute renal failure," Kidney International, vol. 54, pp. 268-274, 1998.

European Search Report, EP 10154030, Jun. 21, 2010, 3 pages.

Communication Pursuant to Article 94(3) EPC, EP 10154030.0, Jul. 2, 2010, 4 pages.

* cited by examiner

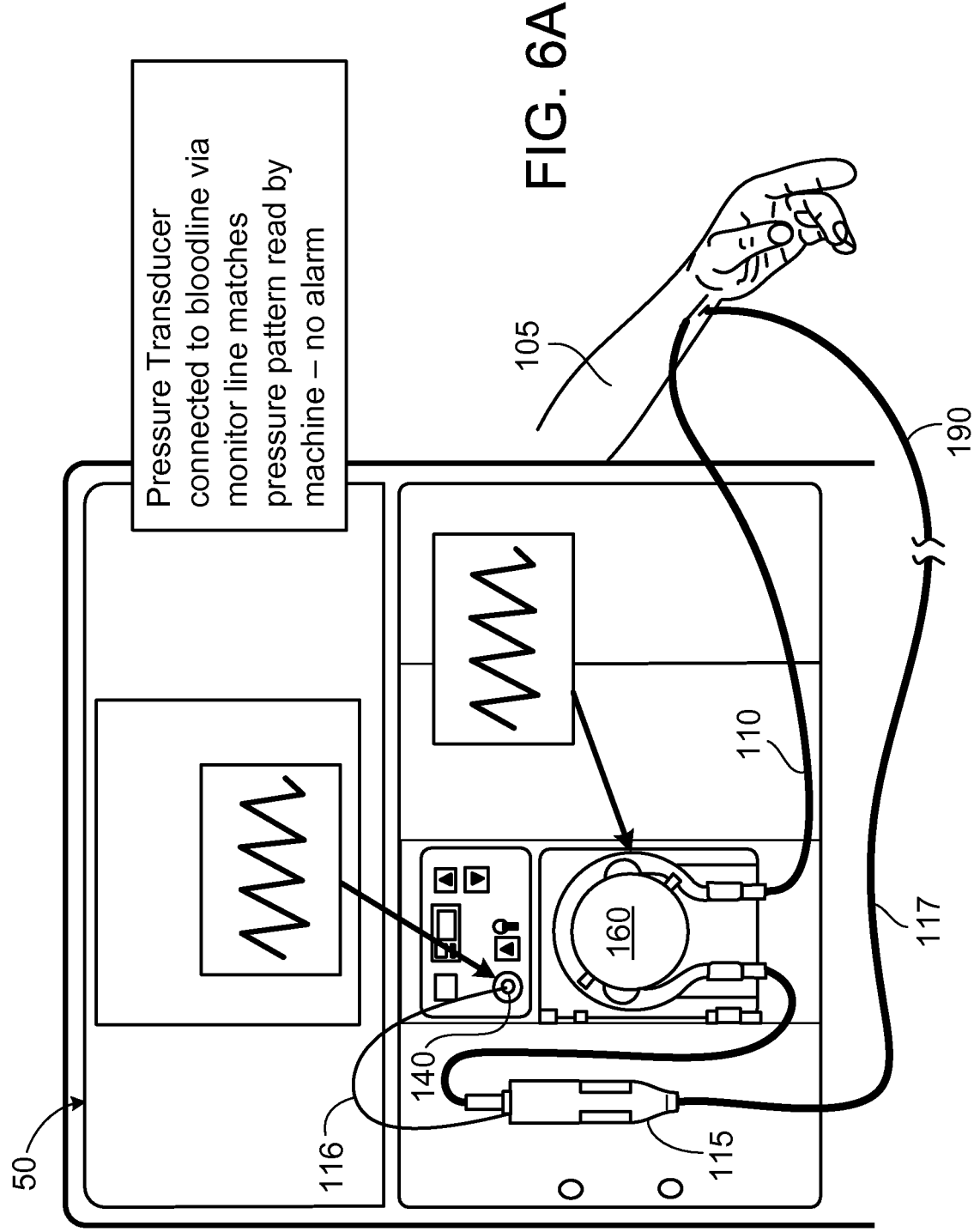

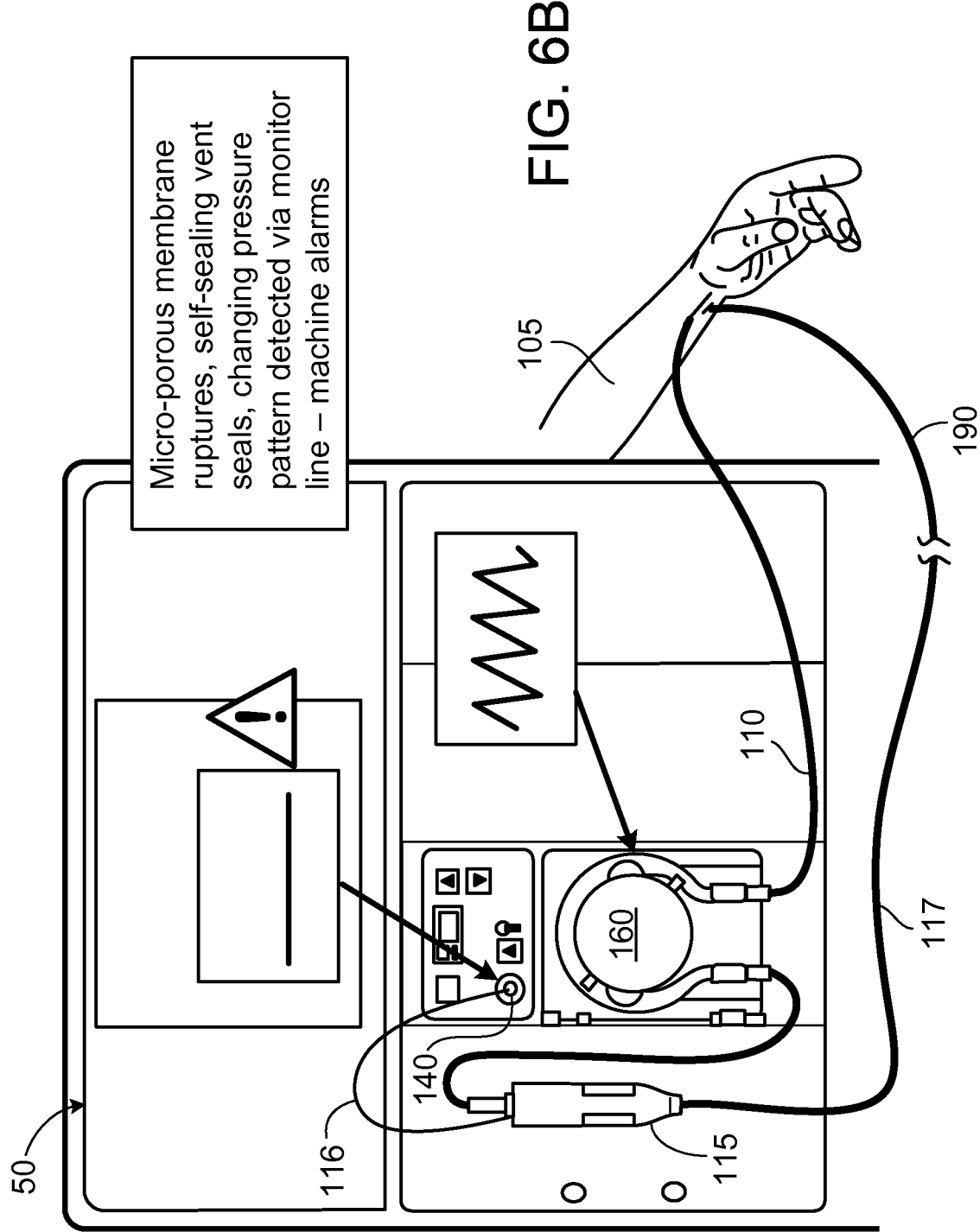

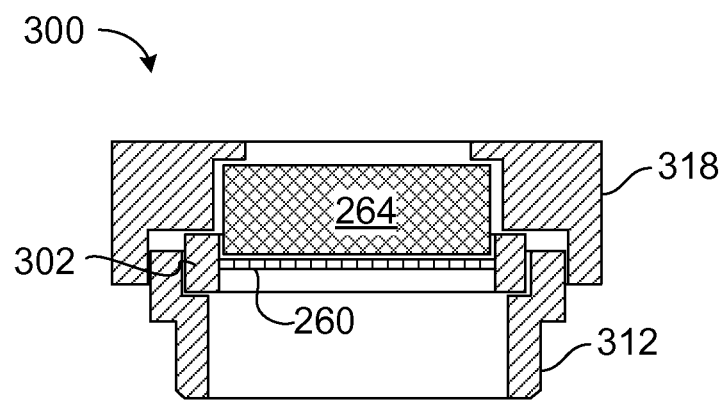
FIG. 12
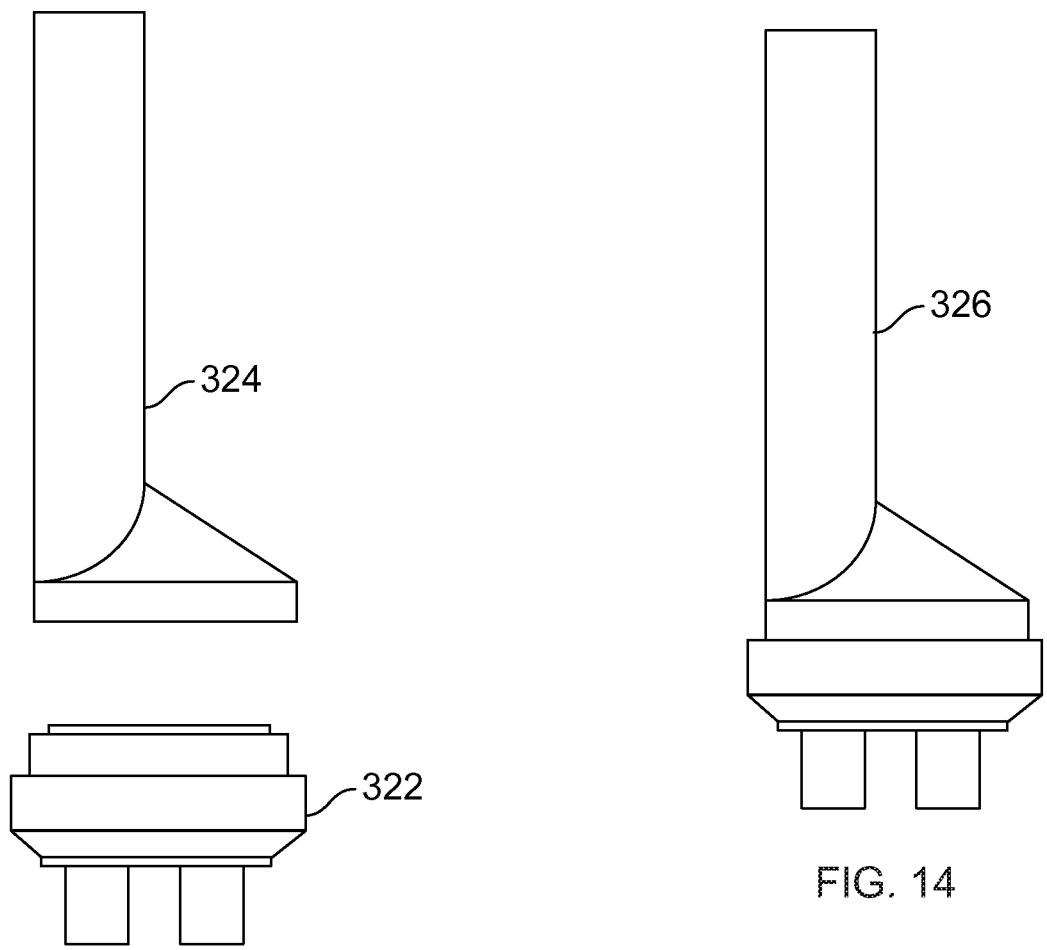
FIG. 13
FIG. 14

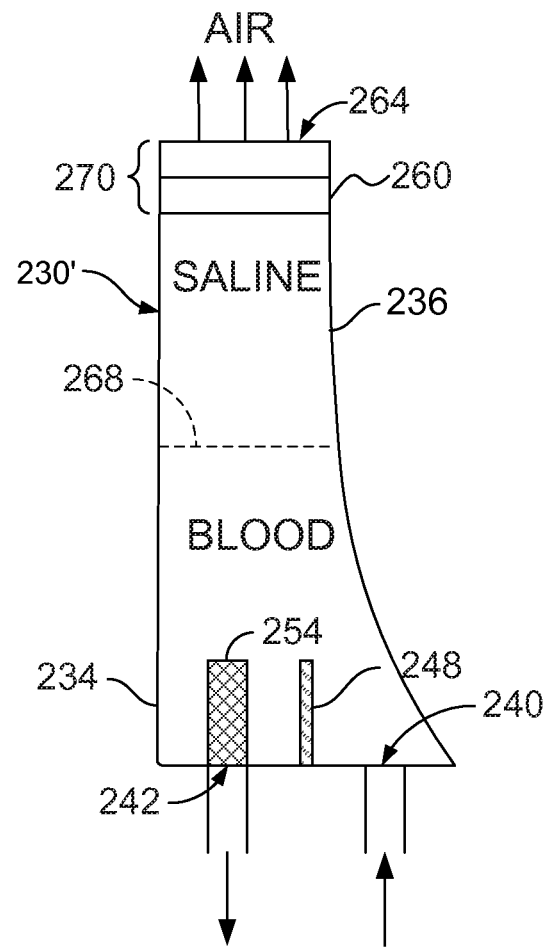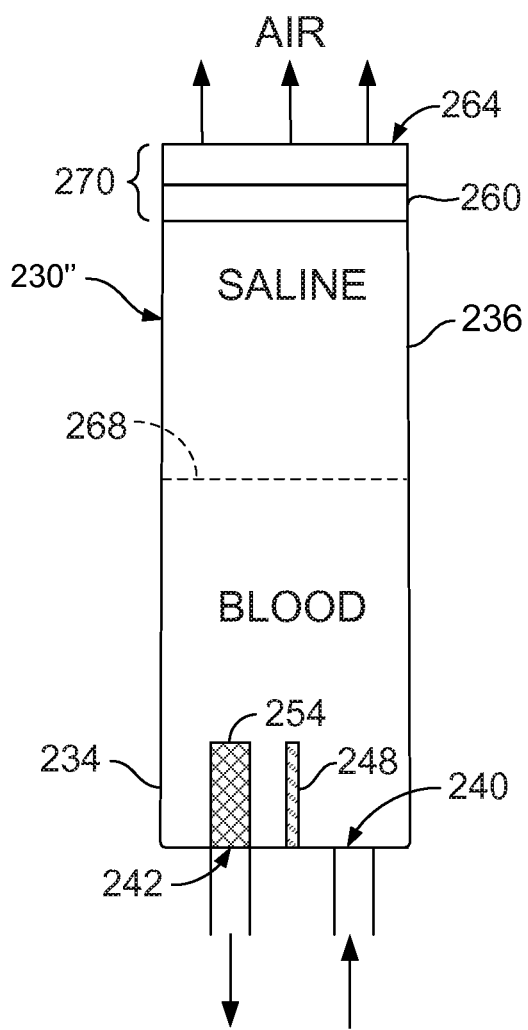
FIG. 22A
FIG. 22B

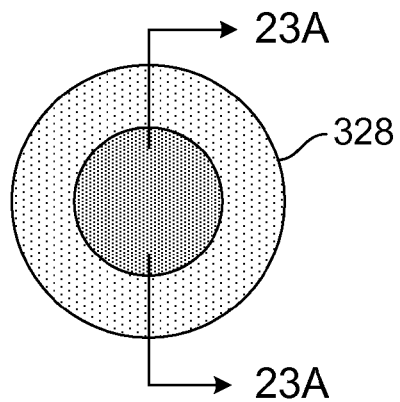
FIG. 23
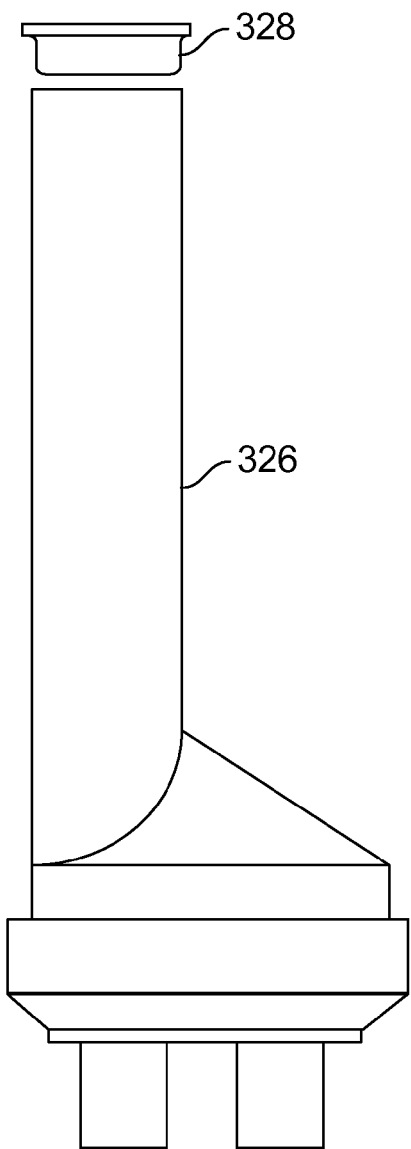
FIG. 25
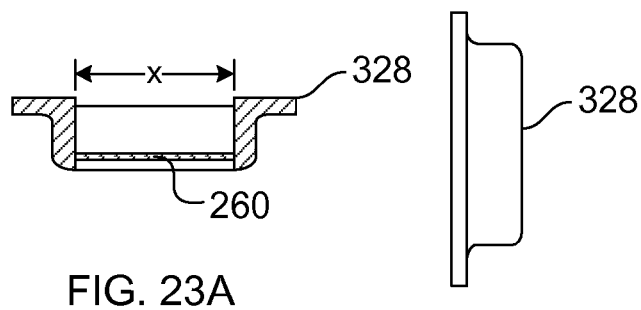
FIG. 23A
FIG. 23B
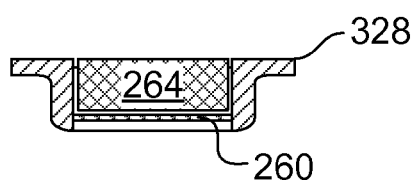
FIG. 24

EXTRACORPOREAL FLUID CIRCUIT AND RELATED COMPONENTS

TECHNICAL FIELD

This disclosure relates to extracorporeal fluid circuits and related components.

BACKGROUND

Hemodialysis removes toxic substances and metabolic waste from the bloodstream using an extracorporeal circuit with components designed to perform ultrafiltration and diffusion on the blood. Before the blood is returned to the body, air bubbles can be removed from the blood to help prevent embolisms.

SUMMARY

In one aspect, an extracorporeal medical fluid circuit component is described. The component includes a vent assembly. A vent structure adjacent to a micro-porous membrane forms the assembly. The vent structure is porous and is capable of changing color when the vent structure is moistened. The component is capable of being used in an extracorporeal medical fluid circuit.

In another aspect, a transducer protector includes a body that defines a fluid pathway. A vent assembly is disposed in the fluid pathway. The vent assembly includes a vent structure and a micro-porous membrane. The vent structure is porous and is capable of changing color when moistened. The transducer protector is capable of being connected in fluid communication with a fluid circuit and a pressure transducer such that the vent assembly inhibits liquid flowing in the fluid circuit from contacting the pressure transducer.

In a further aspect, an extracorporeal medical fluid circuit apparatus, e.g., for removing air from a bodily liquid in extracorporeal circuitry used in a hemodialysis machine, is described. The apparatus includes a chamber having a fluid entry port, and a fluid exit port. The apparatus also includes a vent assembly. The vent assembly includes a micro-porous membrane and a vent structure adjacent to the micro-porous membrane. The vent structure is formed of a porous material that is capable of changing color when moistened. The fluid entry port and the fluid exit port are arranged to allow liquid to pass through the chamber from the entry port to the exit port so as to fill the chamber with the liquid, and the vent assembly is arranged to allow gas to exit the chamber as the liquid passes through the chamber.

In yet another aspect, a system (e.g., a dialysis system, e.g., a hemodialysis system) is described. The system includes a machine body, a pump on the machine body, and fluid circuitry (e.g., tubes) in fluid communication with the pump. The pump is configured to pull fluid from a patient and push fluid through the fluid circuitry. The system also includes a vent assembly in fluid communication with the fluid circuitry. The vent assembly includes a micro-porous membrane and a vent structure adjacent to the micro-porous membrane. The vent structure is formed of a porous material that is capable of changing color when moistened.

Embodiments of the disclosed methods, systems and devices may include one or more of the following features.

In some embodiments, the porous material is capable of swelling when moistened. For example, the porous material can include (e.g., be impregnated with) a swelling agent, such as carboxymethylcellulose, methyl-ethyl-cellulose or other similar swelling agent, that is capable of swelling when moistened.

The vent structure can include a color change additive such as powdered or granulated dye, e.g., food dye, or a pH indicator, such as bromophenol blue.

The vent structure can include about 0.05% by weight to about 2% by weight of a color change additive.

The vent structure can include a polymer such as polyethylene (e.g., high density polyethylene (HDPE), polypropylene, or polystyrene.

The vent structure can include a blend of a polymer (e.g., polyethylene, polypropylene, or polystyrene), a swelling agent (e.g., carboxymethylcellulose), and a color change additive.

The color change additive can be covalently bonded to the swelling agent.

The vent structure can include a blend of a polymer (e.g., polyethylene, polypropylene, or polystyrene), a swelling agent (e.g., carboxymethylcellulose), and a pH indicator (e.g., bromophenol blue).

The pH indicator can be covalently bonded to the swelling agent.

The vent structure can have an average pore size of about 15 microns to about 45 microns.

The micro-porous membrane can have an average pore size of about 0.05 to about 0.45 microns (e.g., about 0.22 microns or about 0.2 microns).

The micro-porous membrane can be hydrophobic.

The extracorporeal medical fluid circuit component can be configured for use in a device adapted to remove air from blood.

The extracorporeal medical fluid circuit component can be configured for use in a transducer protector.

The extracorporeal medical fluid circuit component can be configured for use in a blood circuit.

The dialysis system can include an electro-optical assembly arranged to detect a change in color of the vent structure.

The electro-optical assembly can include a light emitter arranged to emit light towards the vent structure, and a light detector arranged to detect light reflected off of the vent structure.

The system can also include a controller in electrical communication with the electro-optical assembly and the pump. The controller can be configured to halt operation of the pump in response to receiving a signal from the electro-optical assembly indicating that the vent structure has changed color.

The system can also include a speaker, and a controller in electrical communication with the electro-optical assembly and the speaker. The controller can be configured to sound an audible alarm through the speaker in response to receiving a signal from the electro-optical assembly indicating that the vent structure has changed color. The controller can be configured to sound an alarm in response to receiving a signal from the electro-optical assembly indicating that the light detector detected reflected light having a wavelength that falls within a predetermined range (e.g., 440 nm to about 490 nm). The actual wavelength range will match that of the changed vent structure color.

The system can also include a display, and a controller in electrical communication with the electro-optical assembly and the display. The controller can be configured to provide a visual alarm on the display in response to receiving a signal from the electro-optical assembly indicating that the vent structure has changed color.

The system can include a pressure transducer, and a transducer protector disposed between, and in fluid communication with, the fluid circuitry and the pressure transducer. The transducer protector can include the vent assembly.

The system can include a chamber in fluid communication with the fluid circuitry. The chamber can include a fluid entry port and a fluid exit port. The fluid circuitry can be configured to allow liquid to pass through the chamber from the entry port the exit port so as to fill the chamber with the liquid. The vent assembly can be arranged to allow gas to exit the chamber through the vent assembly as the liquid passes through the chamber.

Embodiments can include one or more of the following advantages.

In some embodiments, a visual indication is provided when a membrane failure has occurred.

In some cases, multiple functions such as sealing (e.g., automatic self-sealing) and alerting (e.g., visual indication) are provided in a single device.

In certain embodiments, electro-optical detection helps to ensure that a user is alerted quickly in the event of a membrane failure.

In some embodiments, automatic shut-off of the system occurs when a membrane failure is detected, which can help to inhibit contamination of system components.

Other aspects, features, and advantages are in the description, drawings, and claims.

DESCRIPTION OF DRAWINGS

FIGS. 6A and 6B illustrate a dialysis machine measuring pressure patterns of an extracorporeal blood circuit.

FIG. 12 is a schematic cross-sectional view of a vent assembly.

FIG. 13 is a schematic side view of a chamber and port cap than can be assembled to form a bottom entry/bottom exit chamber.

FIG. 14 is a schematic side view of a bottom entry/bottom exit chamber.

FIGS. 22A, 22B, and 22C are each schematic cross-sectional views of air release chambers.

FIG. 23 is a schematic top view of a filter assembly.

FIG. 23A is a cross-sectional view of the filter assembly of FIG. 23, taken along line 23A-23A.

FIG. 23B is a side view of the filter assembly of FIG. 23.

FIG. 24 is a schematic cross-sectional view of a vent assembly.

FIG. 25 is a schematic side view of a bottom entry/bottom exit chamber and a vent assembly.

DETAILED DESCRIPTION

A fluid circuit, such as an extracorporeal fluid circuit used in filtering blood from a patient during hemodialysis, can be provided with one or more self-sealing/color changing vent assemblies to inhibit (e.g., prevent) fluids flowing within the circuit from coming into contact with the surrounding, external atmosphere and/or coming into contact with, and possibly contaminating, neighboring devices. The self-sealing/color changing vent assemblies can also inhibit (e.g., prevent) foreign particles and organisms from the external atmosphere from coming into contact with liquid flowing within the fluid circuit.

The self-sealing/color changing vent assemblies generally include a micro-porous membrane and a vent structure. In use, the micro-porous membrane is disposed between the vent structure and liquid flowing within a fluid circuit. The micro-porous membrane normally inhibits (e.g., prevents) the liquid flowing within the fluid circuit from contacting the vent structure, while allowing gases, such as air, to pass through. The vent structure is formed of a porous material that normally allows gases to pass through. The vent structure is capable of swelling and changing color when moistened. In the event that the micro-porous membrane ruptures, blood flowing within the fluid circuit will come into contact with the vent structure causing the vent structure to swell and self-seal, inhibiting the passage of fluids, including gases therethrough. As a result of the blood coming into contact with the vent structure, the vent structure also changes color, thereby providing a visual indication that the vent structure has self-sealed.

System Overview

Figure 1:
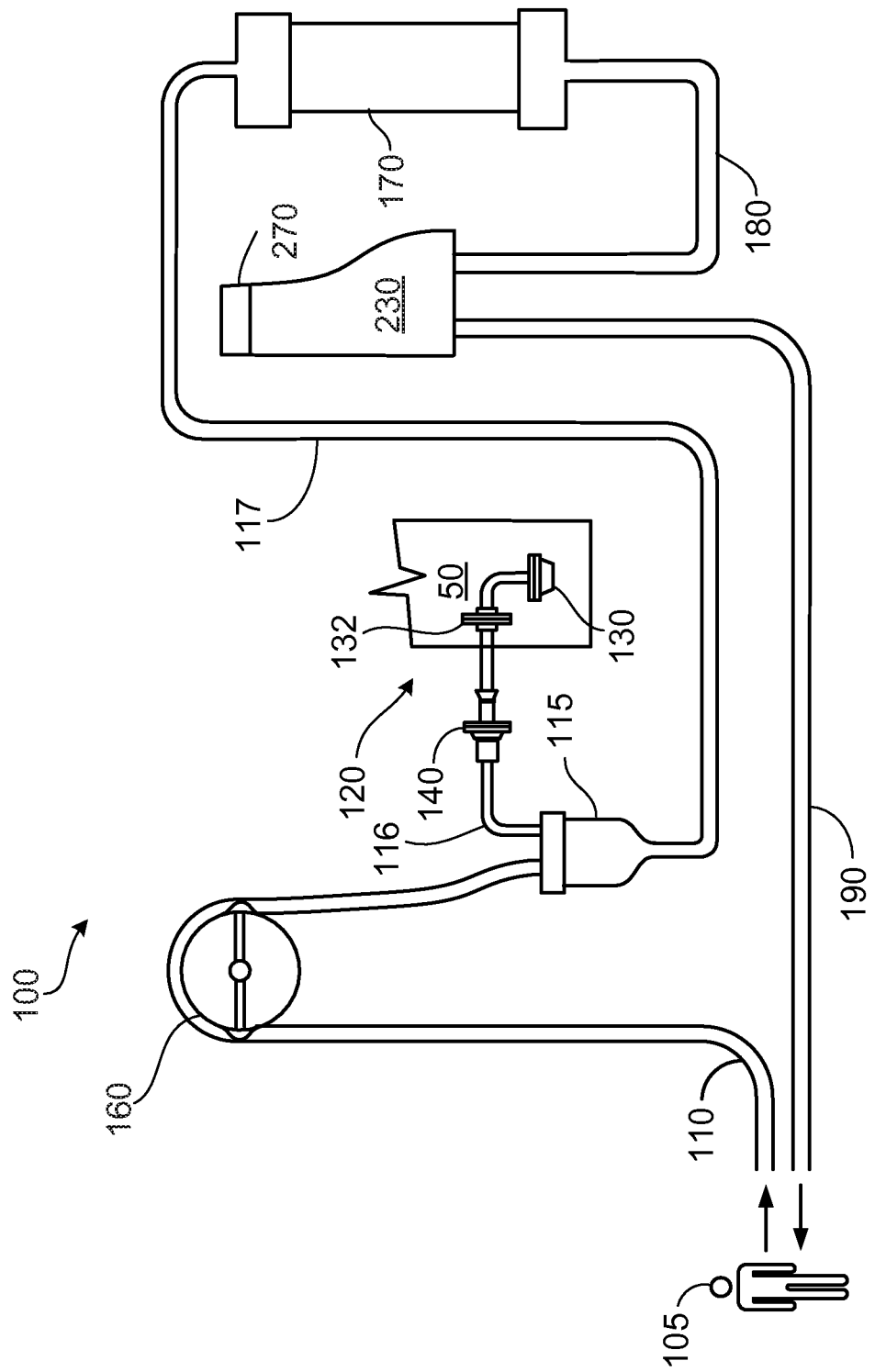
FIG. 1 is a schematic diagram of an extracorporeal fluid circuit for hemodialysis system.

Referring to FIG. 1, an extracorporeal fluid circuit 100 includes tubing through which the blood flows and components for filtering and performing dialysis on the blood. Blood flows from a patient 105 through arterial tubing 110. A pump 160, such as a peristaltic pump, forces the blood to continue along the path through the circuit 100. After exiting the pump, blood drips into a drip chamber 115 where a connecting tube 116 from the drip chamber 115 attaches to an arterial pressure sensor assembly 120 on a hemodialysis machine 50 that determines the pressure of the blood on the arterial side of the circuit 100. The arterial pressure sensor assembly 120 includes a pressure transducer 130, which can be mounted within a dialysis machine 50, so that the pressure of blood flowing through the circuit 100 on the arterial side can be monitored. The arterial pressure sensor assembly 120 also includes an internal transducer protector 132 that is mounted internally to the dialysis machine 50 and in communication with the pressure transducer 130. The internal transducer protector 132 helps to protect the pressure transducer 130, and the dialysis machine 50 from direct contact with blood flowing within the extracorporeal circuit 100. The internal transducer protector 132 includes a microporous membrane 134 that inhibits the flow of liquid while allowing gases (e.g., air) to pass therethrough.

The extracorporeal circuit 100 also includes an external transducer protector 140 that is mounted externally to the dialysis machine 50 between, and in communication with, the drip chamber 115 and the internal transducer protector 132. The external transducer protector 140 carries a self-sealing vent assembly 141 (FIG. 3A) that includes a micro-porous membrane 144 (FIG. 3B) and a liquid activated self-sealing, color-changing vent structure 146 (FIG. 3B). The vent assembly 141 further helps to protect the internal transducer protector 132, the pressure transducer 130, and the dialysis machine 50, from direct contact with blood flowing within the extracorporeal circuit 100. In the event that the micro-porous membrane 144 ruptures, blood will come into contact with the liquid activated self-sealing vent structure 146. The vent structure 146 will seal, and, by sealing, will inhibit (e.g., prevent) the dialysis machine 50 from becoming contaminated, and will allow the machine 50 to detect a failure, e.g., via analysis of pressure patterns, and/or via electro-optical detection of the color changing vent. The vent structure 146 will also change color when exposed to liquid, and thus a visual indication that the vent structure 146 has sealed will be provided.

After exiting the drip chamber 115, the blood then flows through tubing 117 to a dialyzer 170, which separates waste products from the blood.

Figure 7A:
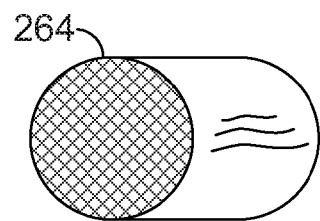
FIG. 7A is a schematic top view of the air release chamber of FIG. 7.
Figure 7:
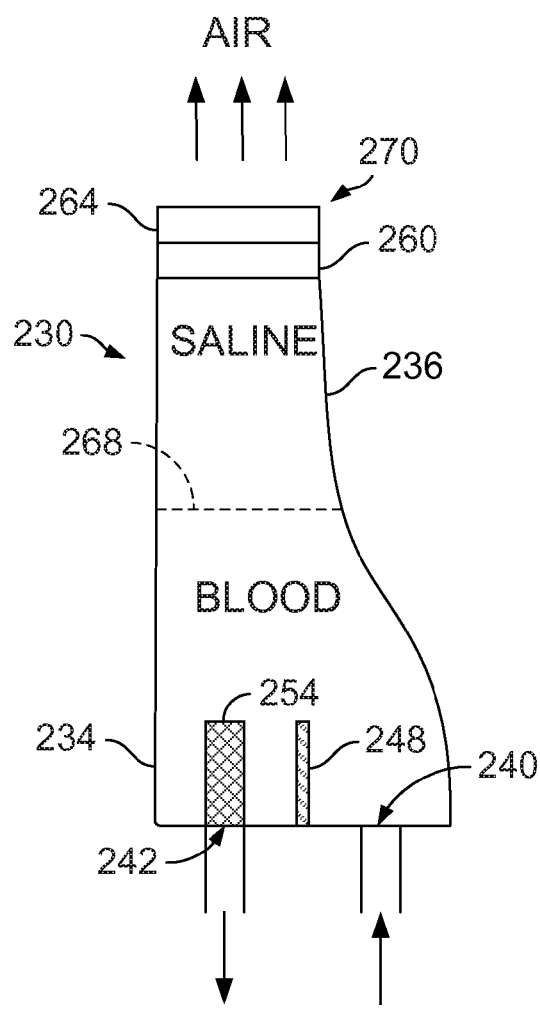
FIG. 7 is a schematic cross-sectional view of an air release chamber with a vent assembly.
Figure 7B:
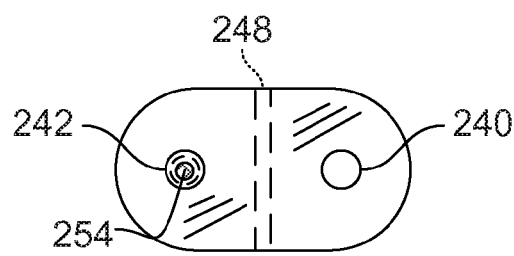
FIG. 7B is a schematic bottom view of the air release chamber of FIG. 7.
Figure 7C:
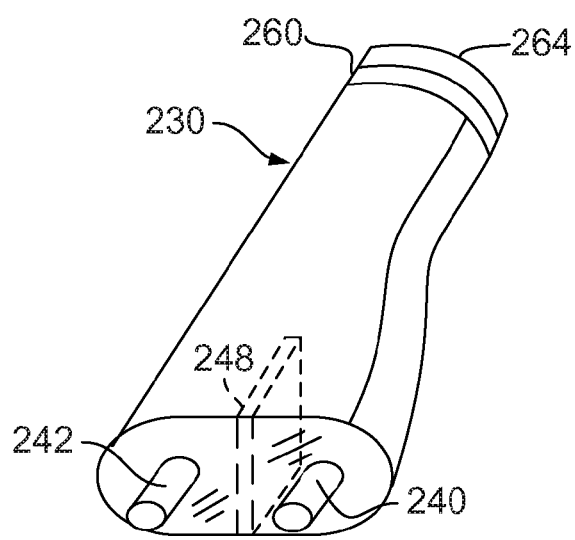
FIG. 7C is a schematic perspective view of the air release chamber of FIG. 7.

After passing through the dialyzer 170, the blood flows through venous tubing 180 towards an air release chamber 230 in which gas (e.g., air) in the blood can escape before the blood continues to the patient 105. During treatment, should air be present in the blood, the blood with air bubbles flows in through the bottom of the air release chamber 230. The upper motion of the blood is impeded by gravity and becomes stagnant, while the air continues to the top of the chamber 230 where it is vented out to the atmosphere through another self-sealing vent assembly 270. The vent assembly 270 of the chamber 230 includes a micro-porous membrane 260 (FIG. 7) and a self-sealing vent structure 264 (FIG. 7). The micro-porous membrane 260 normally operates to inhibit liquids within the chamber 230 from coming into contact with the atmosphere. However, in the event that the micro-porous membrane 260 ruptures, liquid will come into contact with the self-sealing vent structure 264, which will self seal and inhibit (e.g., prevent) the blood from coming into contact with the atmosphere. The self-sealing vent structure 264 of the assembly 270 will also exhibit a color change when it comes in contact with liquid, thereby providing a visual indication that the vent structure 264 has sealed and that fluid flow, including the flow of air, through the vent structure 264 is inhibited.

After leaving the chamber 230, the blood travels through a venous line 190 and back to the patient 105.

External Transducer Protector

Figure 2:
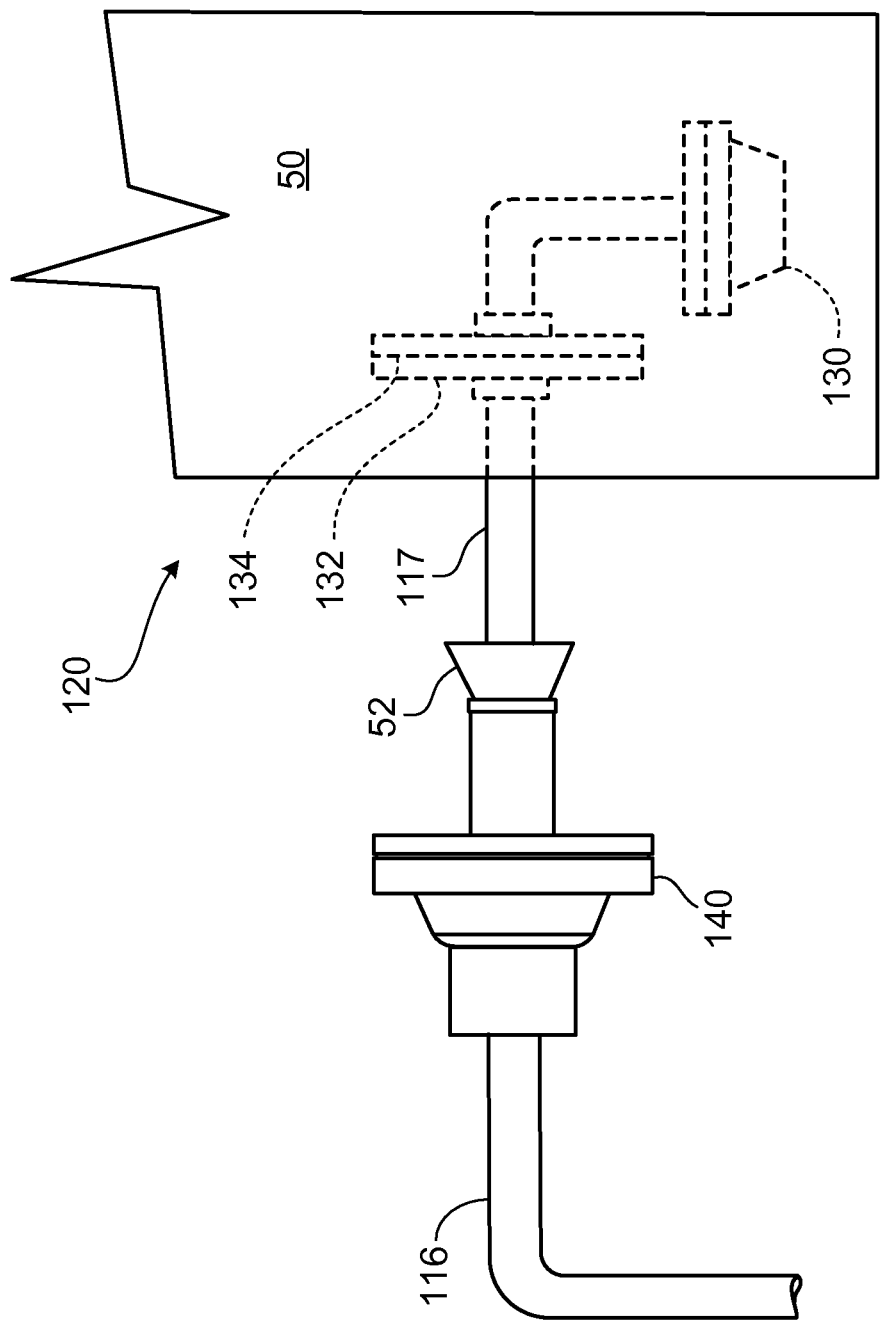
FIG. 2 is schematic view of a pressure sensor assembly and external transducer protector.
Figure 3A:
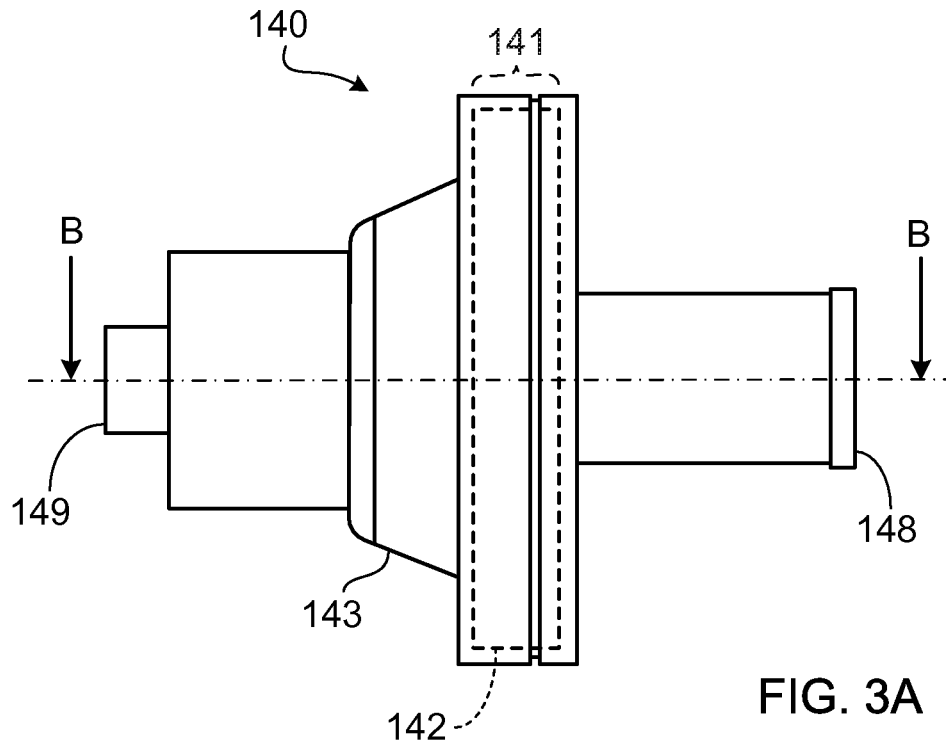
FIG. 3A is side view of an external transducer protector.
Figure 3B:
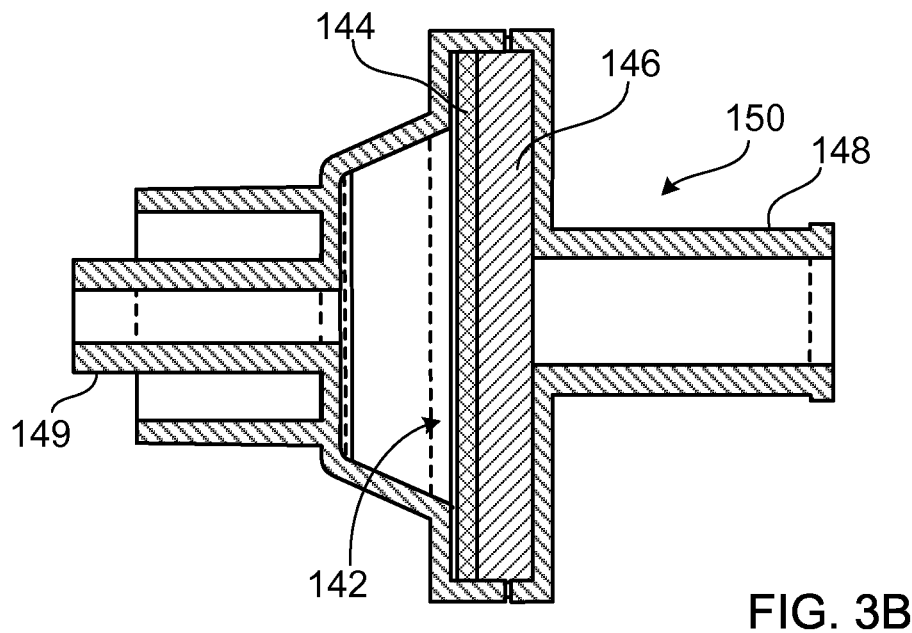
FIG. 3B is a cross-sectional side view of the external transducer protector of FIG. 3A.

Referring to FIGS. 3A and 3B, the external transducer protector 140 includes a body 143 that defines a fluid pathway. The body 143 includes a vent assembly compartment 142 in which the micro-porous membrane 144 and the self-sealing vent structure 146 are disposed. A first open end 148 can be connected to the dialysis machine 50, e.g., via a machine fitment 52 (FIG. 2) and tubing 117, and provides for fluid communication between the pressure transducer 130 and the vent assembly compartment 142. A second open end 149 can be connected to the tubing (e.g., connecting tube 116) of the extracorporeal circuit 100 (FIG. 1) to provide for communication between the vent assembly compartment 142 and blood flowing within the circuit 100. This arrangement allows gas (e.g., air) to pass through the vent assembly 141 from the second open end 149 toward the first open end 148, while inhibiting the passage of blood, and thereby allows the pressure transducer 130 to measure changes in air pressure.

The micro-porous membrane 144 allows gas (e.g., air) to pass through the vent assembly compartment 142, but impedes the flow of liquid, thereby inhibiting or preventing the blood from directly contacting, and possible contaminating, the component (e.g, the internal transducer protector 132, the dialysis machine 50, and the pressure transducer 130) on the opposite side of the vent assembly compartment 142. The micro-porous membrane 144 can also help to inhibit (e.g., prevent) foreign particles and organisms from entering the extracorporeal circuit 100 from the transducer side of the vent assembly compartment 142.

The micro-porous membrane 144 is hydrophobic. For example, in some embodiments, the micro-porous membrane 144 includes a hydrophobic material, such as polytetrafluoroethylene (PTFE) (e.g., expanded polytetraflouroethylene (ePTFE)) backed by a mesh material. In some embodiments, the membrane 144 is a fibrous carrier with a matted and woven layer on top of which ePTFE or other micro-porous material is applied. A suitable membrane has an average pore size of about 0.05 to about 0.45 microns (e.g., about 0.22 microns or about 0.2 microns). Suitable membranes are available from Pall Corporation, East Hills, N.Y., under the Versapor® mark and from W. L. Gore & Associates, Inc., Newark, Del.

The self-sealing vent structure 146 is a solid porous block, having an average pore size of about 5 to about 45 microns, that allows air to pass through the vent assembly compartment 142. In some embodiments, the self-sealing vent structure 146 is formed of a blend of polyethylene (e.g., high density polyethylene (HDPE) and carboxymethylcellulose (CMC), a blend of polystyrene and methyl-ethyl-cellulose or of polypropylene- or polyethylene-based porous material. The vent structure 146 can include about 80% to about 95% by weight high density polyethylene and about 5% to about 20% by weight carboxymethylcellulose.

The self-sealing vent structure 146 also includes a color change additive that is capable of changing color when placed in contact with liquid. The solid porous block (e.g., of polyethylene and carboxymethylcellulose) may be impregnated with the color change additive during manufacture. In some embodiments, the color change additive is covalently bonded to carboxymethylcellulose of the vent structure 146. The color change additive can be a pH indicator, such as bromophenol blue, that changes color when it comes into contact with water. Alternatively or additionally, the color change additive can be a dye, e.g., a food dye, e.g., in powdered or granular form. The vent structure may contain about 0.05% to about 2% by weight color change additive. The vent structure may be formed, for example, by depositing a mixture of high density polyethylene powder, carboxymethylcellulose powder, and powdered dye, in the desired proportions, into a mold and applying heat and pressure to the mixture to form a solid porous block which takes the shape of the mold.

Figure 4A:
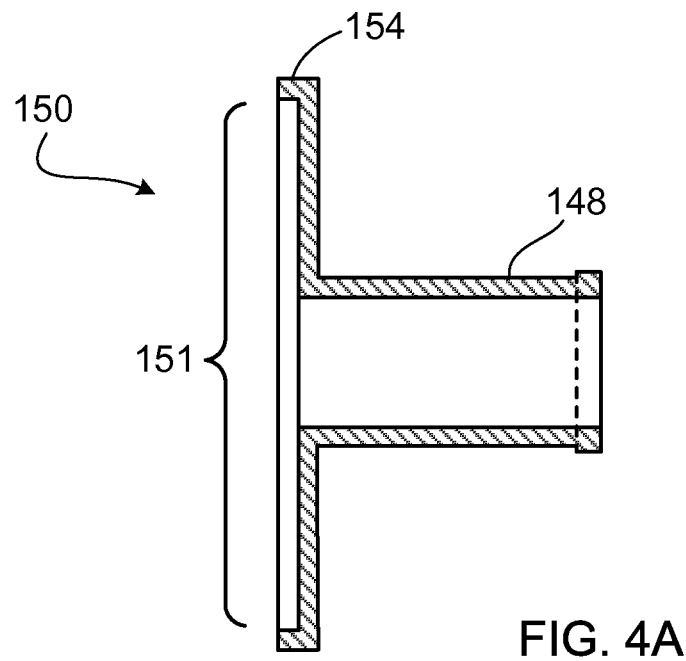
FIG. 4A is a cross-sectional side view of a first part of the external transducer protector of FIG. 3A.
Figure 4B:
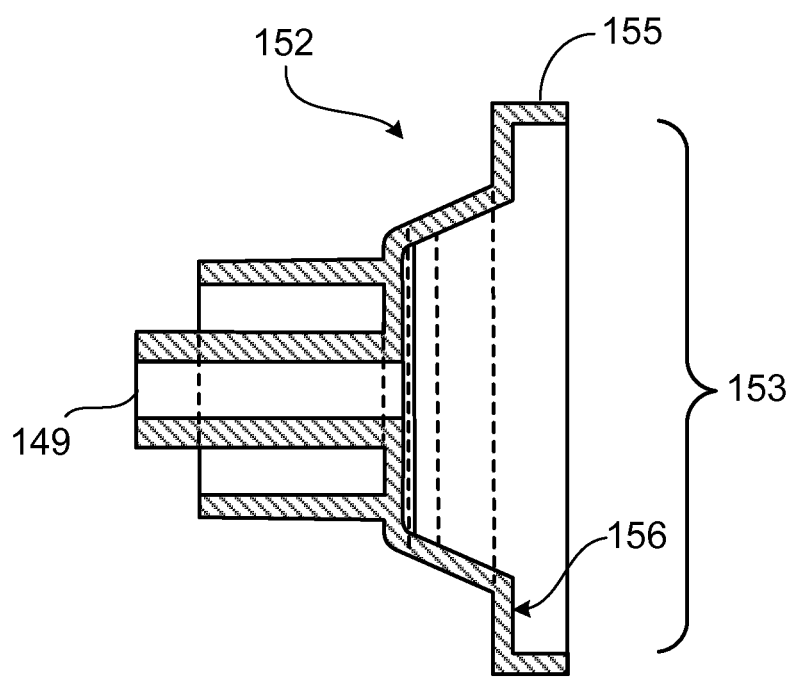
FIG. 4B is a cross-sectional side view of a second part of the external transducer protector of FIG. 3A.

Referring to FIGS. 4A and 4B the body 143 of the external transducer protector 140 can be formed from two parts. As shown in FIG. 4A, a first part 150 defines the first open end 148 and a first portion 151 of the vent assembly compartment 142. As shown in FIG. 4B, a second part 152 defines the second open end 149 and a second portion 153 of the vent assembly compartment 142. The first and second parts 150, 152 of the external transducer protector 140 can be formed of one or more medical grade materials. Plastics, such as polyvinylchloride, polycarbonate, polyolefins, polypropylene, polyethylene or other suitable medical grade plastic can be used because of their ease of manufacturing, ready availability and disposable nature. The first and second parts 150, 152 of the transducer protector can be separately formed, such as by molding (e.g., extruding, blow molding or injection molding). At least one of the first and second parts 150, 152, can be formed of a transparent or clear material so that a change in color of the vent structure 146 can be visually and/or optically observed.

Figure 5A:
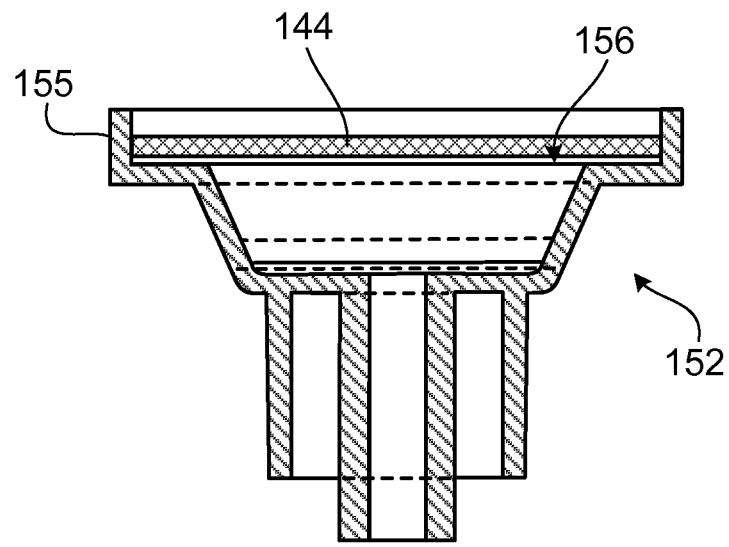
FIGS. 5A-5C are cross-sectional views illustrating the assembly of the external transducer protector of FIG. 3A.
Figure 5B:
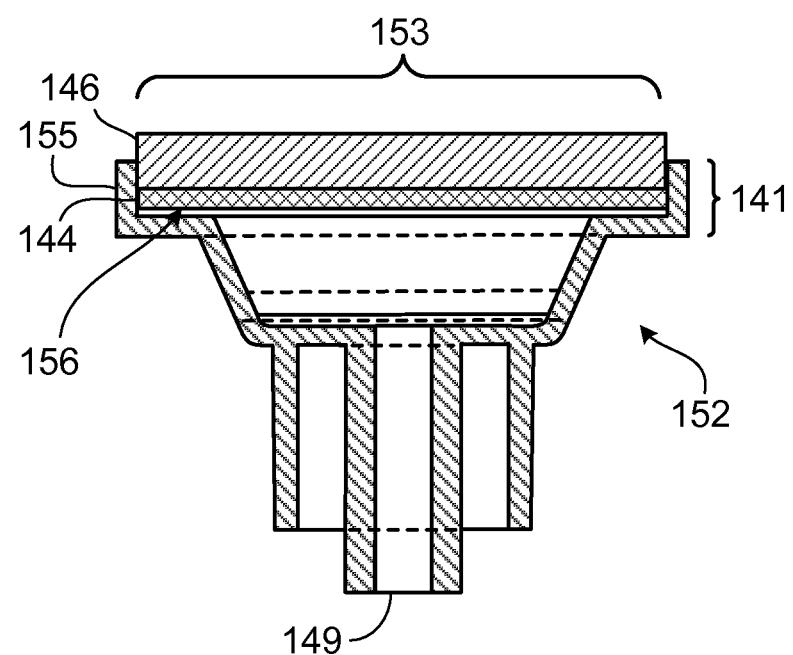
Figure 5C:
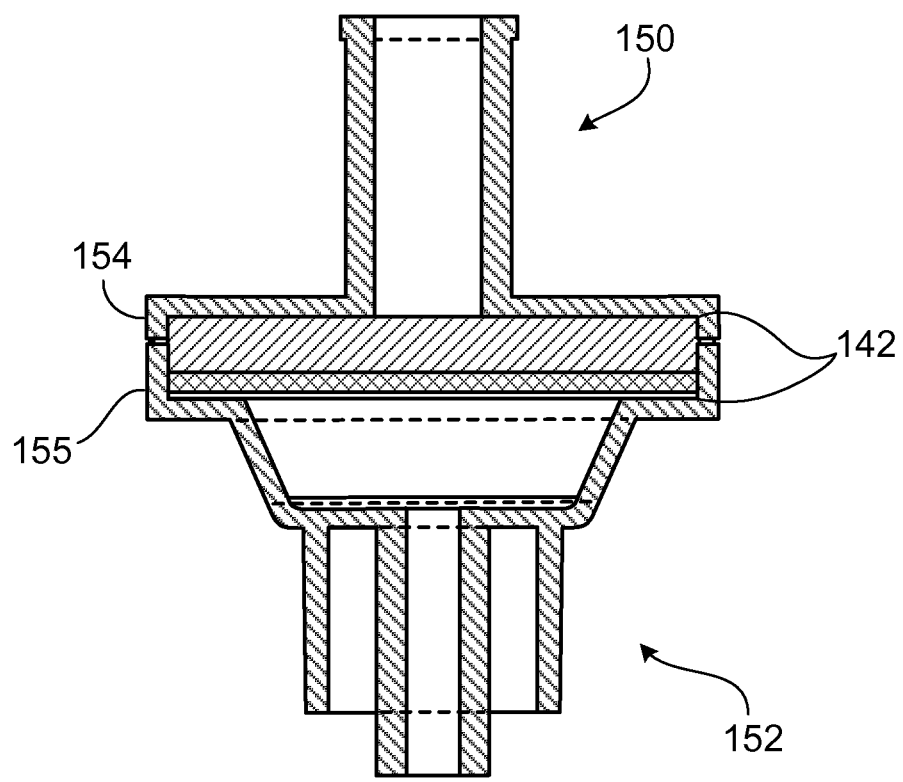

The first and second parts 150, 152 of the external transducer protector 140 each include an associated sidewall 154, 155. The sidewalls 154, 155 of the respective first and second parts 150, 152 help to retain the micro-porous membrane 144 and the self-sealing vent structure 146 within the vent assembly compartment 142 following assembly. As illustrated in FIGS. 5A-5C, the external transducer protector 140 is assembled by first inserting the micro-porous membrane 144 into the second part 152 in a position in which the micro-porous membrane 144 is disposed within the second portion 153 of the vent assembly compartment 142. In this position, as shown in FIG. 5A, the micro-porous membrane 144 is seated against a ledge 156 that is defined by the second part 152. The micro-porous membrane 144 can be dimensioned such that a press-fit is provided between the micro-porous membrane 144 and the sidewall 155 of the second part 152 of the external transducer protector 140. Next, as illustrated in FIG. 5B, the self-sealing vent structure 146 is positioned adjacent the micro-porous membrane 144 in a position in which the self-sealing vent structure 146 is partially disposed within the second portion 153 of the vent assembly compartment 142. The self-sealing vent structure 146 can also be dimensioned such that a press-fit is provided between the vent structure 146 and the sidewall 155 of the second part 152 of the external transducer protector 140. Then, as illustrated in FIG. 5C, the first part 150 can be connected to the second part 152 of the external transducer protector 140 such that the respective sidewalls 154, 155 of the first and second parts 150, 152 of the external transducer protector 140 together define the vent assembly compartment 142. The first and second parts 150, 152 of the external transducer protector 140 can be bonded to each other, such as by welding, adhering (e.g., with epoxy), solvent bonding, mating threaded connections or other suitable method.

In use, if a rupture of the micro-porous membrane 144 occurs, blood flowing in the extracorporeal fluid circuit 100 may come into contact with the vent structure 146 causing the vent structure 146 to seal and change color, and, by sealing will change pressure to the pressure transducer 130 in the dialysis machine 50. Referring to FIGS. 6A and 6B, pressure can be read out and displayed through the electronics of the dialysis machine 50. Dynamic pressure pulse variations may take place, and will be transmitted through tubing sections 116, 117 (FIG. 2) to the pressure transducer 130, for a continuous pressure measurement. The measured pressure pattern is compared to a machine pressure pattern, which is determined as a function of pump operation. If there is a variance between the measured pressure pattern and the machine pressure pattern automatic shut-off can occur and/or an alarm can be sounded. If, for example, the micro-porous membrane 144 ruptures, thereby allowing liquid (e.g., blood) to contact the self-sealing vent structure 146, the vent structure 146 will self seal and inhibit (e.g., prevent) fluid, including gases, from passing. As a result, as illustrated in FIG. 6B, the pressure transducer 130 will sense a change in the pressure pattern (e.g., a diminished pressure pulse), which the associated dialysis machine electronics will interpret as a possible membrane rupture.

Air Release Chamber

Referring to FIGS. 7, 7A, 7B and 7C, the air release chamber 230 is substantially hollow for filling with a liquid. The chamber 230 can be used for removing gas (e.g., air bubbles) from blood. The chamber 230 has a bottom region 234 and a top region 236, where the bottom and top are relative to the chamber's orientation during use. An entry port 240 and an exit port 242 are in the bottom region 234 of the chamber 230. In some implementations, a dam 248 is between the ports 240, 242. The dam 248 extends at least part way from one side wall to an opposite side wall. In some implementations, the dam 268 contacts each side wall so that all fluid entering entry port 240 flows over the top of the dam 248 before flowing out the exit port 242. In some implementations, a clot filter 254 is positioned adjacent to the exit port 242. Fluid flows through the clot filter 254 prior to flowing out of the exit port 242. In some implementations, the clot filter 245 has a porosity of about 50 microns to about 500 microns.

The ports 240, 242 are holes in the chamber 230 which can be in fluid communication with tubular shaped extensions. The extensions are able to be connected to tubes, such as by pressure fitting or bonding. The extensions can be integrally formed with the chamber 230 or subsequently attached to the chamber 230, such as by bonding or welding.

At the top region 236 of the chamber 230 is the self-sealing vent assembly 270. The self-sealing vent assembly 270 includes the micro-porous membrane 260 and the vent structure 264. The assembly with the vent structure 264 and micro-porous membrane 260 may provide reduced condensation or minimize condensation on the micro-porous membrane 260. The micro-porous membrane 260 allows gas (e.g., from air bubbles in the blood) to vent from the chamber 230. Pores in the micro-porous membrane 260 are small enough to keep foreign particles and organisms from entering the chamber 230 from the outside air.

In some implementations, the membrane 260 includes a hydrophobic material, such as polytetrafluoroethylene (PTFE) (e.g., expanded polytetraflouroethylene (ePTFE)). In some embodiments, the membrane 260 is a fibrous carrier with a matted and woven layer on top of which PTFE or other micro-porous material is applied. The hydrophobic micro-porous membrane 260 keeps liquid from leaking out of the chamber 230 when the chamber 230 is substantially filled with liquid and allow air to pass through. A suitable membrane has an average pore size of about 0.05 microns to about 0.45 microns (e.g., about 0.22 microns, about 0.2 microns). Suitable membranes are available from Pall Corporation, East Hills, N.Y., under the Versapor® mark and from W. L. Gore & Associates, Inc., Newark, Del.

The vent structure 264 is a solid porous block, having an average pore size of about 15 microns to about 45 microns, that allows air to pass through and escape from the chamber. The vent structure 264 is also a self-sealing vent structure. In some implementations, the vent structure 264 is formed of a blend of polyethylene (e.g., high density polyethylene (HDPE) and carboxymethylcellulose (CMC), a blend of polystyrene and methyl-ethyl-cellulose or of polypropylene- or polyethylene-based porous material. The vent structure 264 can include about 80% to about 95% by weight high density polyethylene and about 5% to about 20% by weight carboxymethylcellulose.

The vent structure 264 also includes a color change additive that is capable of changing color when placed in contact with liquid. The solid porous block (e.g., of polyethylene and carboxymethylcellulose) that forms the vent structures 264 may be impregnated with the color change additive during manufacture. In some embodiments, the color change additive is covalently bonded to the vent structure. For example, the color change additive can include a pH indicator, such as bromophenol blue, that is covalently bonded to carboxymethylcellulose of the vent structure 264. Alternatively or additionally, the color change additive can include a dye, e.g., a food dye, e.g., in powdered or granular form. The vent structure may contain about 0.05% to about 2% by weight color change additive. The vent structure may be formed, for example, by depositing a mixture of high density polyethylene powder, carboxymethylcellulose powder, and powdered food dye, in the desired proportions, into a mold and applying heat and pressure to the mixture to form a solid porous block which takes the shape of the mold.

When the vent structure 264 comes into contact with liquid, e.g., humidity or moisture, the swelling agent (e.g., cellulose component, e.g., carboxymethylcellulose) of the vent structure expands, thereby closing off the pores in the polymer component (e.g., high density polyethylene) of the vent structure 264. In addition, the color of the vent structure 264 will change giving a visual indication that liquid has come into contact with the vent structure 264. The vent structure 264 is mounted adjacent to and just above the membrane 260 so that the hydrophobic membrane 260 is located between the vent structure 264 and the chamber 230. The vent structure 264 inhibits (e.g., prevents) condensation from accumulating on and contacting the membrane 260. In some embodiments, the vent structure 264 directly contacts the membrane 260. The vent structure 264 can be substantially disc shaped or can be another shape that is compatible with a chamber on which the vent structure 264 is mounted. In embodiments, the vent structure 264 is about 0.1 mm to about 10 mm thick.

When the chamber 230 is filled with blood, inhibiting (e.g., preventing) the protein in the blood from accumulating on the membrane 260 can maintain the hydrophobic characteristic of the membrane 260. Whole blood can be kept from the membrane 260 by providing a barrier between the blood and the membrane 260, such as a liquid barrier 268, as described further below. The height of the chamber 230 is sufficient to maintain this barrier 268 and inhibits (e.g., prevents) the liquid above the barrier 268 from substantially mixing with liquid below the barrier 268.

The chamber is formed of a material suitable for medical devices, that is, a medical grade material. Plastics, such as polyvinylchloride, polycarbonate, polyolefins, polypropylene, polyethylene or other suitable medical grade plastic can be used because of their ease of manufacturing, ready availability and disposable nature. The chamber is formed, such as by molding, for example, extruding, blow molding or injection molding. The chamber can be formed of a transparent or clear material so that the liquid flowing through the chamber can be observed.

Figure 8:
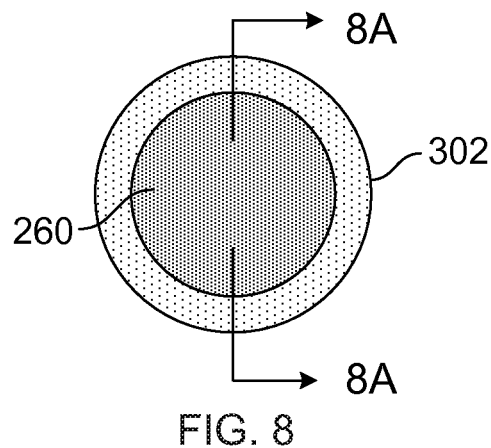
FIG. 8 is a schematic top view of a hydrophobic filter assembly.
Figure 8A:
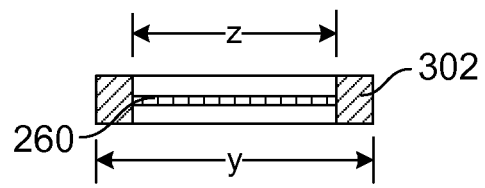
FIG. 8A is a schematic cross-sectional view of the hydrophobic filter assembly of FIG. 8, taken along line 8A-8A.
Figure 9:
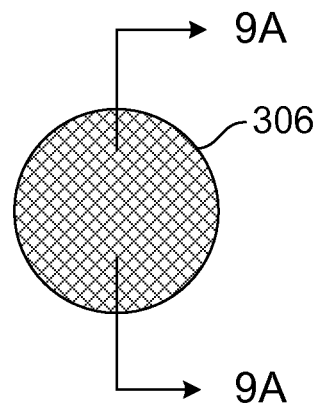
FIG. 9 is a schematic top view of a vent structure.
Figure 9A:
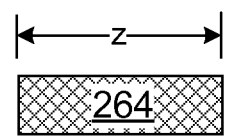
FIG. 9A is a cross-sectional view of the vent structure of FIG. 9, taken along line 9A-9A.

The construction of the vent assembly 270 is described with respect to the following figures. Referring to FIGS. 8 and 8A, a ring 302 holds the micro-porous membrane 260 within its inner diameter. The ring can be formed of plastic, such as one of the plastics described herein. The micro-porous membrane 260 can be insert-molded into the ring 302. That is, the micro-porous membrane 260 can be placed into a mold and held in place. The plastic for the ring 302, which can be polyethylene, polystyrene or another other suitable material, is then injected into a mold to form the ring 302. The ring 302 has an inner diameter z and an outer diameter y. Referring to FIGS. 9 and 9A, the vent structure 264 has a diameter of z.

Figure 10:
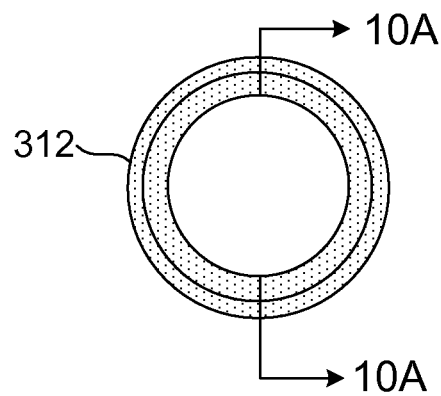
FIG. 10 is a schematic top view of an insert.
Figure 10A:
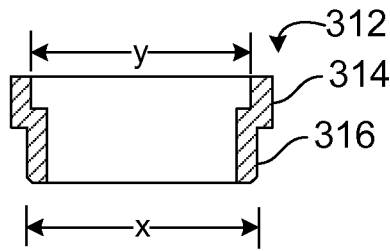
FIG. 10A is a cross-sectional view of the insert of FIG. 10, taken along line 10A-10A.
Figure 10B:
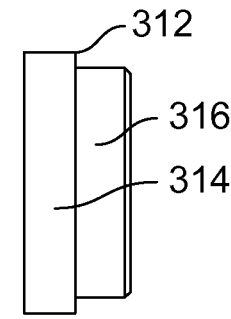
FIG. 10B is a side view of the insert of FIG. 10.

Referring to FIGS. 10 and 10A, an insert 312 is configured to hold the ring 302 and the vent structure 264. The insert 312 has a first portion 314 and a second portion 316. The first portion 314 has a greater outer diameter and greater inner diameter than the outer diameter and inner diameter of the second portion 316. In some embodiments, the inner diameter of the first portion 314 is y and the outer diameter of the second portion 316 is x. The transition between the first portion 314 and the second portion 316 forms a ledge. The insert 312 can be formed of the same plastic or a different material from the plastic ring.

Figure 11:
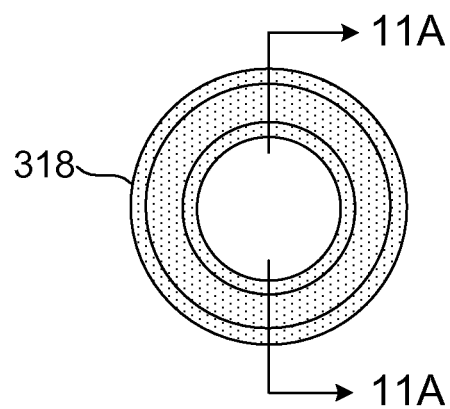
FIG. 11 is a schematic top view of a retainer.
Figure 11A:
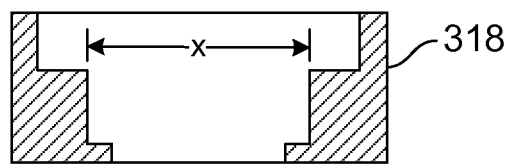
FIG. 11A is a cross-sectional view of the retainer of FIG. 11, taken along line 11A-11A.

Referring to FIGS. 11 and 11A, a retainer 318 is configured to hold the ring 302, the vent structure 264 and the insert 312. In some embodiments, the retainer 318 has a constant outer diameter, that is, the outer diameter does not change from one end of the retainer 318 to the other. In some embodiments, the retainer 318 has three unique inner diameters. Near the top (as shown in the figure) of the retainer 318, the inner diameter is the greatest and in some embodiments, the inner diameter is equal to or just slightly greater than the outer diameter of the first portion 314 of the insert 312. Near the bottom of the retainer 318, the retainer 318 can have an inner diameter that is less than z, or less than the diameter of the vent structure 264. Between the bottom and the top of the retainer 318, the inner diameter can be about equal to x, that is, about equal to or slightly greater than the outer diameter of the second portion 316 of insert 312.

Referring to FIG. 12, an assembly 300 can be formed from the ring 302, vent structure 264, insert 312 and retainer 318. The retainer 318 holds the vent structure 264 so that the portion of the retainer with an the inner diameter that is less than the vent structure's diameter inhibits (e.g., prevents) the vent structure 306 from escaping. The ring 302 is within the inner diameter of the retainer 318 and adjacent to the vent structure 264. In some embodiments, the ring 302 has sufficient height that the vent structure 264 can be seated within the inner diameter of the ring 302. The first portion 314 of the insert 312 fits between the outer diameter of the ring 302 and the inner diameter of the retainer 318. The retainer 318 can be bonded to the insert 312, such as by welding, adhering, solvent-bonding or other suitable method. The second portion 316 of the insert 312 forms a shank that is sized to fit into a chamber, as described further herein.

Figure 15:
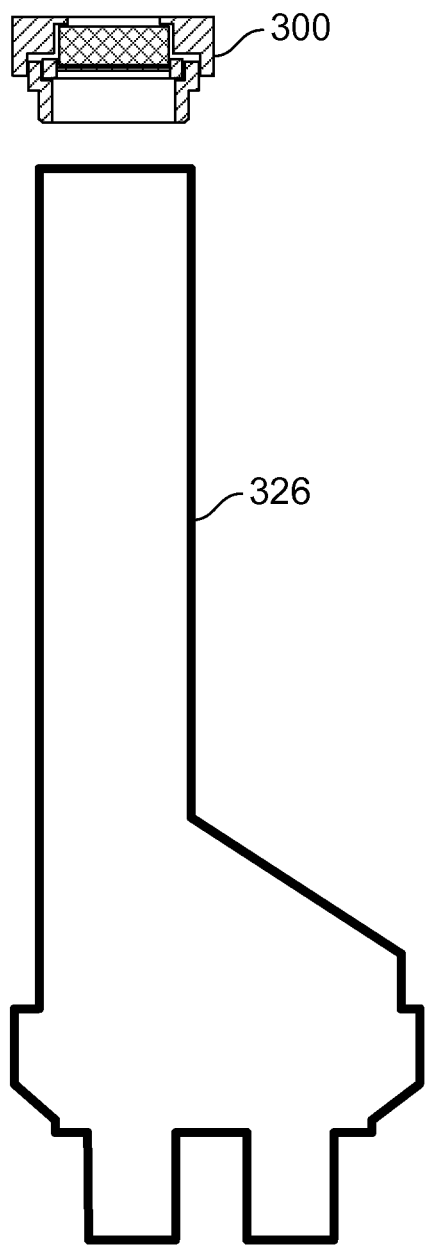
FIG. 15 is a schematic cross-sectional view of a bottom entry/bottom exit chamber and a vent assembly.
Figure 16:
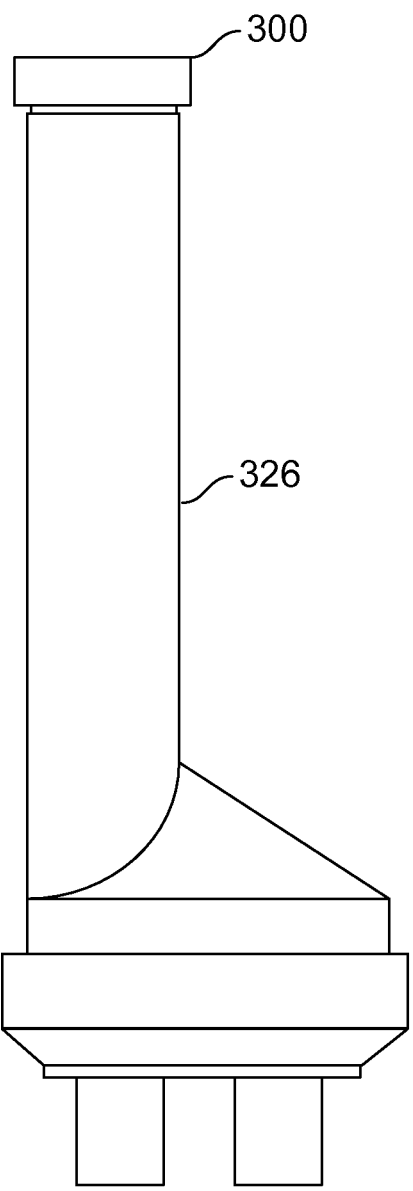
FIG. 16 is a schematic side view of a bottom entry/bottom exit chamber with a vent assembly.

Referring to FIG. 13, the chamber can be formed from two parts. A two port cap 322 can form a bottom of the chamber. A gravity chamber 324 can form the top of the chamber. Referring to FIG. 14, when the cap 322 and gravity chamber 324 are brought together, they form a chamber body 326. The top of the chamber body 326 is sized so that the shank of the assembly 300 can be fit into the chamber body 326, as shown in FIGS. 15 and 16. The chamber body 326 and the assembly 300 can be sealed together, such as by welding, adhering, solvent-bonding or other suitable method.

Although the vent assemblies described herein are shown as cylindrical, the assembly can have other shapes as well, such as rectangular, polygon, triangular or other suitable cross sectional shapes. Also, the vent assembly can have a threaded portion so that the assembly can be, for example, screwed into the air release chamber. Alternatively, the vent assembly can be welded, adhered with epoxy or otherwise fastened to the top of the chamber.

Methods of Operation

Figure 17:
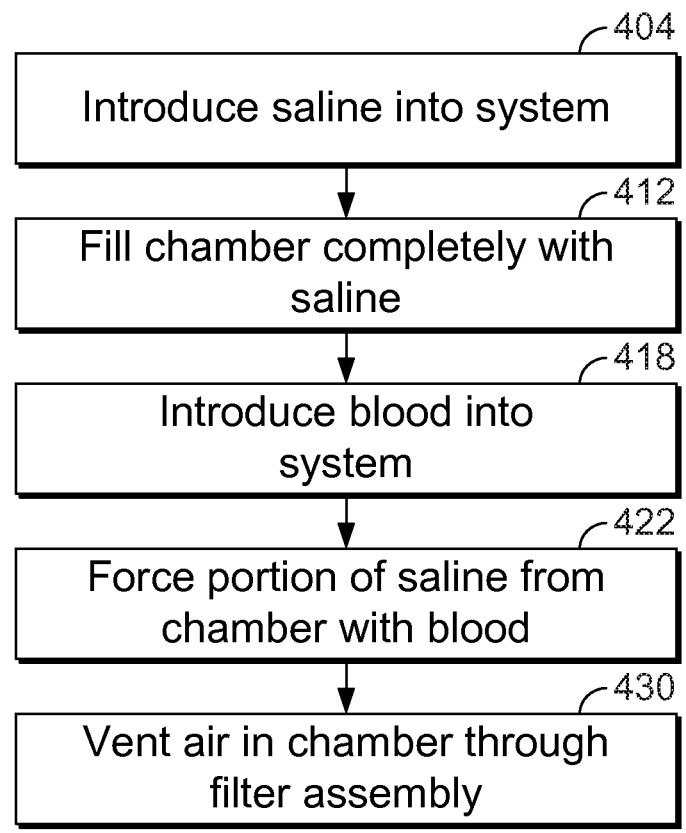
FIG. 17 is a flow diagram for using an air release chamber in an extracorporeal circuit.

Referring to FIGS. 1 and 17, the air release chamber 230 is in line in the extracorporeal fluid circuit of a system for fluid filtration and air removal. A first liquid that is compatible with the liquid to be filtered (the second liquid) is introduced into the system to prime the system (step 404). In hemodialysis, the first liquid is a blood compatible solution, such as saline. The pump 160 forces the saline through the circuit 100. The saline flows through the arterial tubing 110 to the arterial pressure sensor assembly 120 so that the pressure of the liquid flowing through the circuit 100 on the arterial side can be monitored, as described above. The saline then flows to the dialyzer 170. Next, the saline, or the first liquid, flows through the entry port 242 of the chamber 230 and fills the chamber (step 412). To fill the chamber completely, venous line 190 can be clamped to create a positive pressure once the saline is introduced into the chamber 230. Air is forced out the top of the chamber 230 and through the micro-porous membrane 260 and vent structure 264 as saline fills the chamber 230. The saline contacts the membrane 260 and the chamber 230 is substantially free of air once the chamber 230 is completely filled. However, the saline does not exit through the membrane 260, because the membrane 260 is hydrophobic. After the venous line 190 is unclamped, the saline exits through the exit port of the chamber and out the venous line 190.

Figure 18:
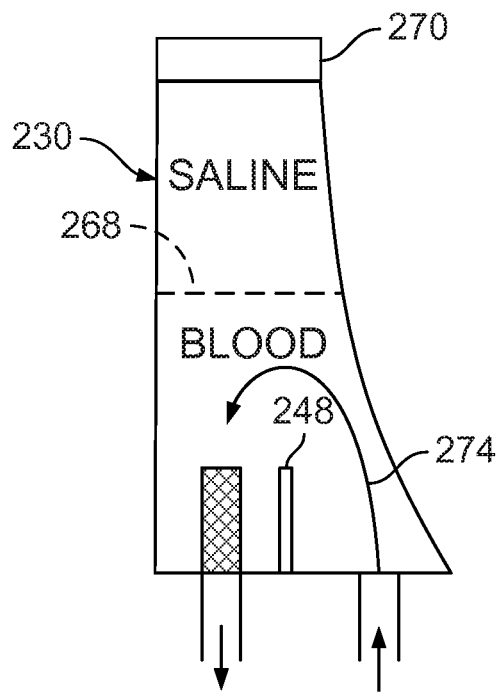
FIG. 18 is a schematic diagram of the blood flow path through an air release chamber.

The second liquid, such as a bodily fluid, for example, blood, is then introduced into the system (step 418). The blood follows the same route as the saline and, for the most part, pushes the saline through the circuit 100. When the blood enters the chamber 230, the blood forces the saline at the bottom of the chamber 230 through the exit port (step 422). However, the blood does not displace all of the saline within the chamber 230. Because of the height of the chamber 230, the blood enters the chamber 230 and only traverses part of the height of the chamber 230 before flowing back down along flow path 274 to the exit port (as shown in the air release chamber formed of transparent material in FIG. 18). An interface 268 between the saline and the blood delineates the furthest extent of most of the blood within the chamber 230. The interface 268 between the blood and saline can visually be observed and stretches across the entire width of the chamber. Because blood and saline are not immiscible, there is some amount of mixing between the two fluids around the interface 268.

The saline keeps the blood from contacting the filter 260. However, a percentage of blood can be present in the saline without hindering the operation of the circuit 100. That is, the saline need not be completely free from blood for the air release chamber 230 to both allow gas (e.g., from air bubbles in the blood) to vent from the circuit 100 and retain the liquid in the circuit 100. The solution that is mostly saline substantially protects the membrane 260 from becoming coated with protein. If the chamber 230 is sufficiently elongated, the blood does not mix with the saline at the top portion of the chamber 230 because the saline remains relatively stagnant as the blood flows through the chamber 230.

Any unbound gas, or air, that is in the blood, such as air that is introduced by the dialyzer 170 or air that comes out of solution from the blood, rises as tiny air bubbles within the blood and saline until the air eventually vents out through the vent assembly 270, including the micro-porous filter 260 and the vent structure (step 430). With a dam 248 inside of the chamber 230, the blood travels up and over the dam 248 rather than straight across the bottom of the chamber 230 out the exit port 242. By directing the flow of blood upwards, the blood with air is not able to flow in and directly back out of the chamber 230 without flowing upwards to at least a height greater then the height of the dam 248. The surface area of the dam 248 and the inner walls of the chamber 230 enables air, including microbubbles, to separate from the blood and exit the circuit 100 through the micro-porous membrane 260.

Throughout the circuit, the blood flows without there being a substantial air-blood interface. Although the blood does not come into contact with air and thus clotting is less likely to occur, the blood can pass through an optional filter in the chamber. In some implementations, after exiting the chamber, the blood passes by or through one or more sensors, such as temperature or air detecting sensors.

Other Embodiments

While certain embodiments have been described above, other embodiments are possible.

Figure 19:
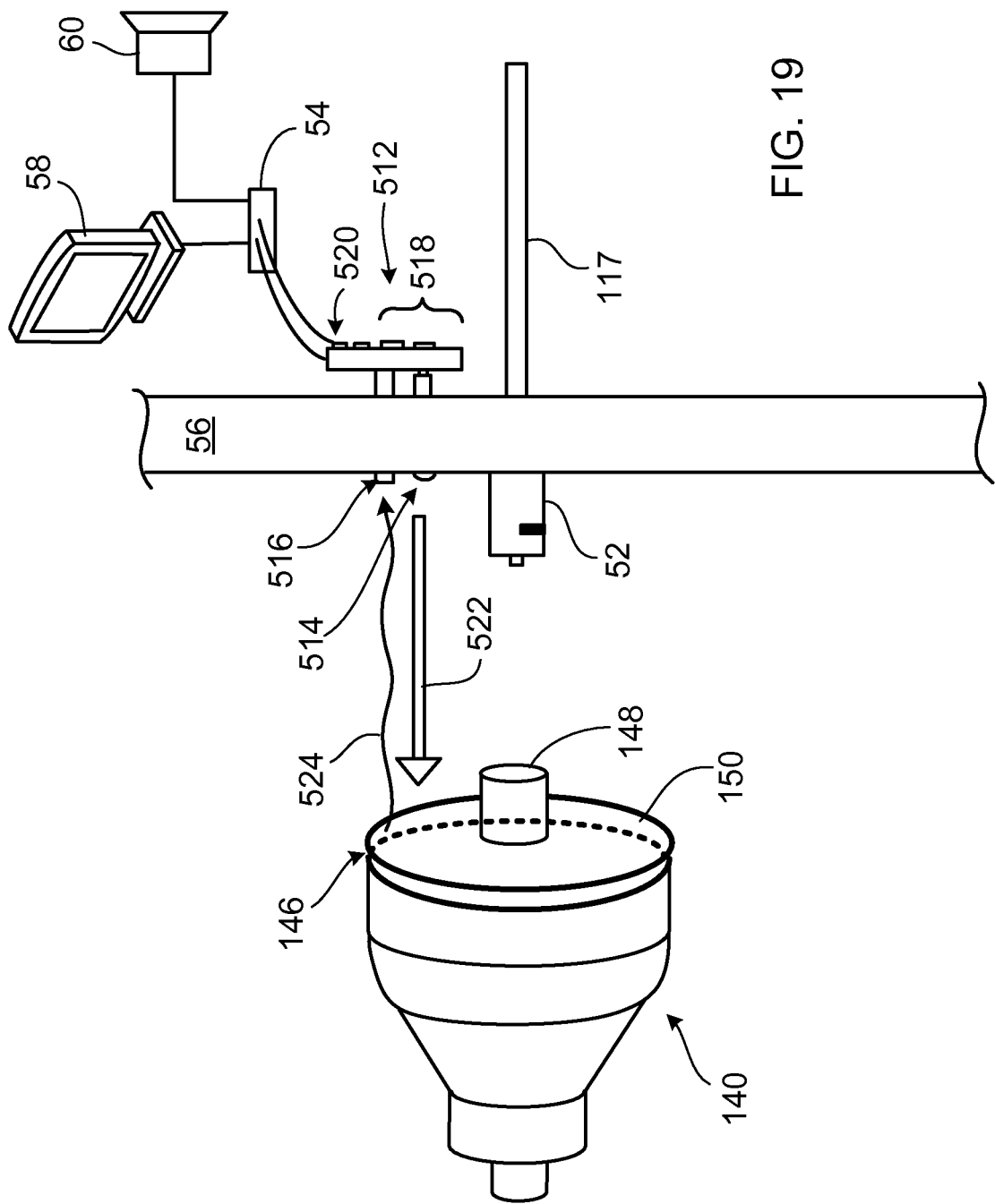
FIG. 19 is a schematic diagram illustrating an electro-optical assembly for detecting color changes of a vent structure of a transducer protector.

In some embodiments, a color change of a color changing self-sealing vent structure can be detected electro-optically. For example, as illustrated in FIG. 19, an electro-optical assembly 510 is provided for detecting a change in color of the vent structure 146 of the external transducer protector 140. The electro-optical assembly 510 includes a printed circuit board 512 on which a light emitter 514 (e.g., a light-emitting diode (LED), e.g., a white LED) and a light detector 516 are mounted. The printed wiring board 512 also carries driver electronics 518 for driving the light emitter 514 and the light detector 516, and interface electronics 520 which provide for electrical communication with a host controller 54 of the dialysis machine 50.

As shown in FIG. 19, the electro-optical assembly 510 is mounted in a wall 56 of the dialysis machine 50 in a position proximate the machine fitment 52. The electro-optical assembly 510 is arranged such that, when the first open end 148 of the external transducer protector 140 is connected to the machine fitment 52, the light emitter 514 and the light detector 516 are adjacent to the vent structure 146 within the external transducer protector 140. The first part 150 of the external transducer protector 140 is optically clear (e.g., molded from an optically clear polymer, e.g., polycarbonate) so that a color change will be visible and optically detectable through the first part 150.

Under the control of the host controller 54, the light emitter 514 emits light 522 towards the vent structure 146. At least a portion of the light is reflected back toward the light detector 516. The light detector 516 is tuned to receive reflected light 524 corresponding to the wavelength of the color changing vent structure 146. For example, where the vent structure 146 is capable of changing from substantially white to a shade of blue when moistened, the light detector 516 is tuned to receive reflected light having a wavelength of about 440 nm to about 490 nm. In response to detecting the reflected light 524, the light detector 516 produces a corresponding electrical signal which is processed and delivered, via the interface electronics, to the host controller 54.

The host controller 54 can be configured to provide a visual alert (e.g., on a display 58 in electrical communication with the controller 54), sound an audible alarm (e.g., through a speaker 60 in electrical communication with the controller 54) and/or automatically shut-off the dialysis machine 50 (e.g., halt operation of the pump 160) in response to receiving a signal from the electro-optical assembly 510 indicating that color change has been detected.

Figure 20:
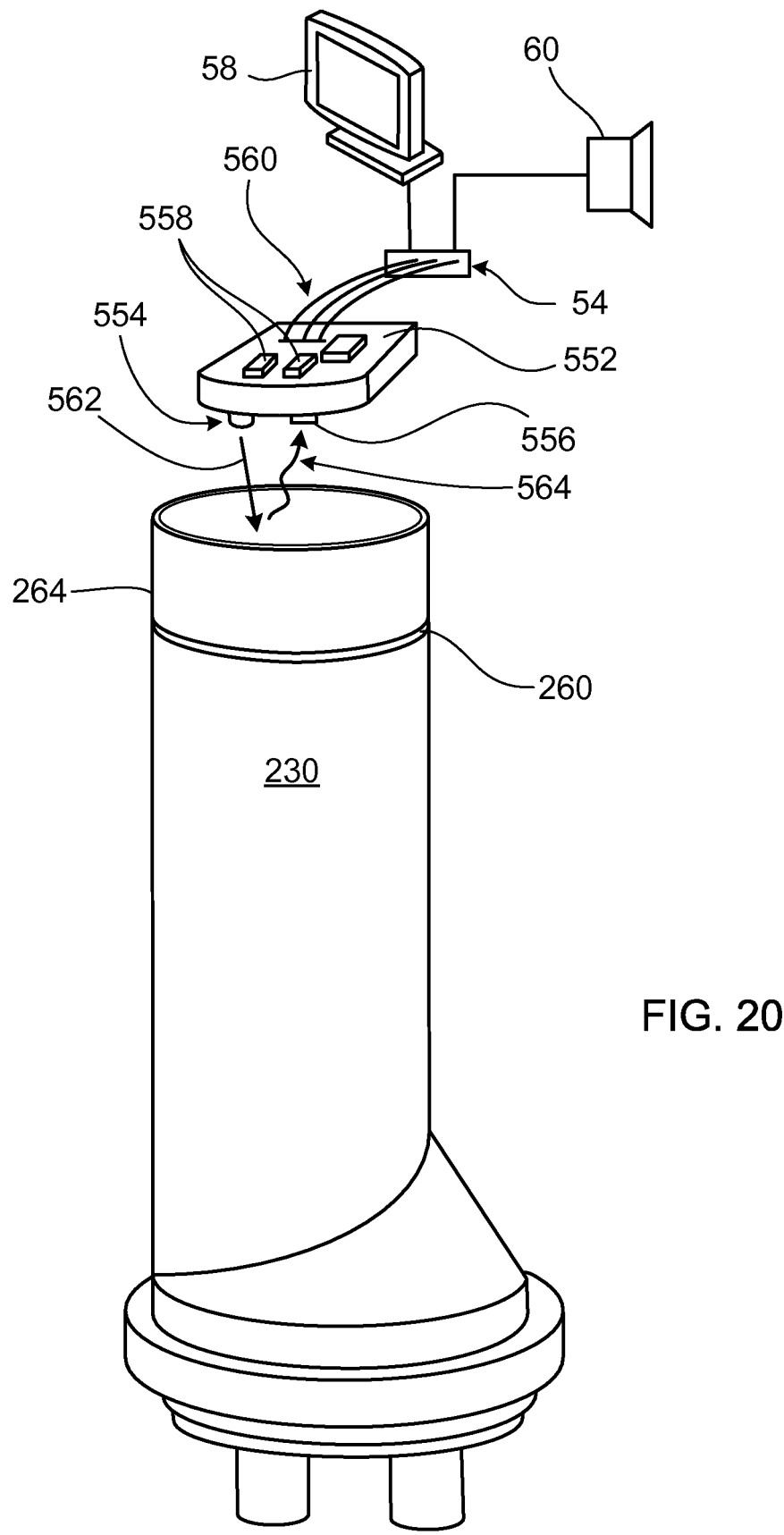
FIG. 20 is a schematic diagram illustrating an electro-optical assembly for detecting color changes of a vent structure connected to an air release chamber.

Alternatively or additionally, an electro-optical assembly 550 can be provided for detecting a color change of the vent structure 264 that is in communication with the air release chamber 230. Referring to FIG. 20, the electro-optical assembly 550 includes a printed circuit board 552 on which a light emitter 554 (e.g., a light-emitting diode (LED), e.g., a white LED) and a light detector 556 are mounted. The printed wiring board 552 also carries driver electronics 558 for driving the light emitter 554 and the light detector 556, and interface electronics 560 which provide for electrical communication with the host controller 54 of the dialysis machine 50. The electro-optical assembly 550 is mounted, e.g., to the dialysis machine 50, in a position proximate the chamber 230 and arranged such that the light emitter 554 and the light detector 556 are adjacent to the vent structure 264.

Under the control of the host controller 54, the light emitter 554 emits light 562 towards the vent structure 264. At least a portion of the light is reflected back toward the light detector 556. The light detector 556 is tuned to receive reflected light 554 corresponding to the wavelength of the color changing vent structure 264. For example, where the vent structure 264 is capable of changing from substantially white to a shade of blue when moistened, the light detector 556 is tuned to receive reflected light having a wavelength of about 440 nm to about 490 nm. In response to detecting the reflected light 554, the light detector 556 produces a corresponding electrical signal which is processed and delivered, via the interface electronics, to the host controller 54 where it is evaluated to determine the status (i.e., whether or not a color change has occurred) of the vent structure 264.

The host controller 54 can be configured to provide a visual alert (e.g., on a display 58 in electrical communication with the controller 54), sound an audible alarm (e.g., through a speaker 60 in electrical communication with the controller) and/or automatically shut-off the dialysis machine 50 (e.g., halt operation of the pump 160) in response to receiving a signal from the electro-optical assembly 550 indicating that a color change has been detected.

Figure 21:
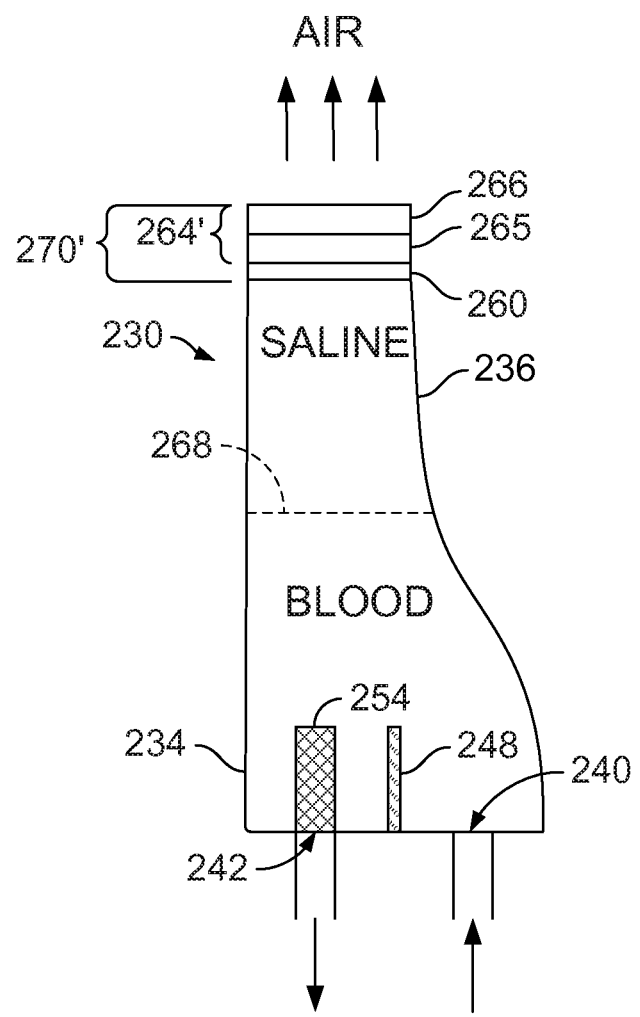
FIG. 21 is a schematic cross-sectional view of an air release chamber with a vent assembly having a multilayer vent structure.

In some implementations, the vent assembly can include a multilayer self-sealing vent structure, where different layers of the vent structure have differing self-sealing (e.g., swelling) characteristics and where one or more of the layers are capable of changing color when exposed to moisture. For example, FIG. 21 shows (in cross-section) a vent assembly 270' including a multilayer self-sealing vent structure 264'. The multilayer self-sealing vent structure 264' includes a first porous layer 265 disposed adjacent the micro-porous membrane 260, and a second porous layer 266 disposed adjacent to the first porous layer 265. The first porous layer 265 is a solid porous block, having an average pore size of about 5 microns to about 45 microns, e.g., about 10 microns. In some embodiments, the first porous layer 265 can be formed of polyethylene (e.g., high density polyethylene (HDPE)), polystyrene, or of polypropylene- or polyethylene-based porous material. Such materials are available from Porex Corporation, Fairburn, Ga. The first porous layer 265 is about 3 mm to about 5 mm thick, e.g., about 4 mm thick. In some embodiments, the first porous layer 265 can be self-sealing. In some embodiments, for example, the first porous layer 265 may include a relatively small amount of carboxymethylcellulose, e.g., about 0% to about 10% by weight carboxymethylcellulose. The second porous layer 266 is a solid porous block, having an average pore size of about 15 to about 45 microns, e.g., about 30 microns. The second porous layer 266 is about 3 mm to about 5 mm thick, e.g., about 4 mm thick. The second porous layer 266 is self-sealing, and is relatively more responsive to the presence of moisture that the first porous layer 265; i.e., the second porous layer 266 has a greater propensity to self-seal (e.g., swell) in the presence of moisture than the first porous layer 265. In some embodiments, the second porous layer 266 is formed of a blend of polyethylene (e.g., high density polyethylene (HDPE)) and carboxymethylcellulose (CMC), a blend of polystyrene and methyl-ethyl-cellulose or of polypropylene- or polyethylene-based porous material.

The second porous layer 266 also includes a color change additive that is capable of changing color when placed in contact with liquid. The solid porous block (e.g., of polyethylene and carboxymethylcellulose) that forms the second porous layer 266 may be impregnated with the color change additive during manufacture. In some embodiments, the color change additive is covalently bonded to the second porous layer 266. For example, the color change additive can include a pH indicator, such as bromophenol blue, that is covalently bonded to carboxymethylcellulose of the second porous layer 266. Alternatively or additionally, the color change additive can include a dye, e.g., a food dye, e.g., in powdered or granular form. Second porous layer 266 may contain about 0.05% to about 2% by weight color change additive. The second porous layer 266 may be formed, for example, by depositing a mixture of high density polyethylene powder, carboxymethylcellulose powder, and powdered food dye, in the desired proportions, into a mold and applying heat and pressure to the mixture to form a solid porous block which takes the shape of the mold.

During use, condensation can, for example, form within the vent assembly. The first porous layer 265 allows for a small amount of condensation to be compensated for without activation of the self-sealing property of the second porous layer 266. The first porous layer 265, being relatively less responsive to the presence of moisture (i.e., as compared to the second porous layer 266) slows the progression of moisture from within the chamber 230 toward the second porous layer 266. The first porous layer 265 provides additional surface area (e.g., within pores) where condensation can be pulled out of the air exiting the vent assembly 270' before it reaches self-sealing, second porous layer 266. Thus, small amounts of humidity and moisture (e.g., condensation) from within the air release chamber 230 can be compensated for without triggering closure of the vent structure 264'. In the event that the second porous layer 266 is exposed to moisture (e.g., in the event of a membrane rupture), the second porous layer 266 will seal, thereby closing off the vent structure 264'. The second porous layer 266 will also change color when exposed to liquid, and thus a visual indication that the vent structure 146 has sealed will be provided.

In some embodiments, the first porous layer 265 may also include a color change additive, such as described above, that is capable of changing color when placed in contact with liquid. Thus, a visual indication can be provided when first porous layer 265 is exposed to moisture. This may help to provide an early warning of a possible membrane failure. In some embodiments, the shape of the air release chamber is approximately elongate. In some implementations, such as those shown in FIGS. 7 and 22A, the bottom region 234 of the chamber 230, 230' is wider than the top region 236, such that the chamber 230, 230' has a quasi-conical shape or a flare at the bottom. In some implementations, such as those shown in FIG. 22B, the top and bottom dimensions of the chamber 230" are approximately equal so that the chamber 230" has a rectangular or cylindrical shape. The bottom region 234 can also be narrower than the top region 236. If the ports 240, 242 are in the bottom surface of the chamber, the bottom surface has a sufficiently large dimension to accommodate the ports 240, 242 as well as any tubes coupled to the ports for directing fluid into and out of the chamber. For example, if the tubing has an outer diameter of 6.25 mm, the bottom surface is at least 12.5 mm wide. The chamber 230 is sized to maintain the liquid barrier 268. In some implementations, the chamber 230 is at least about two inches in height, (e.g., about three to about four inches).

Figure 22C:
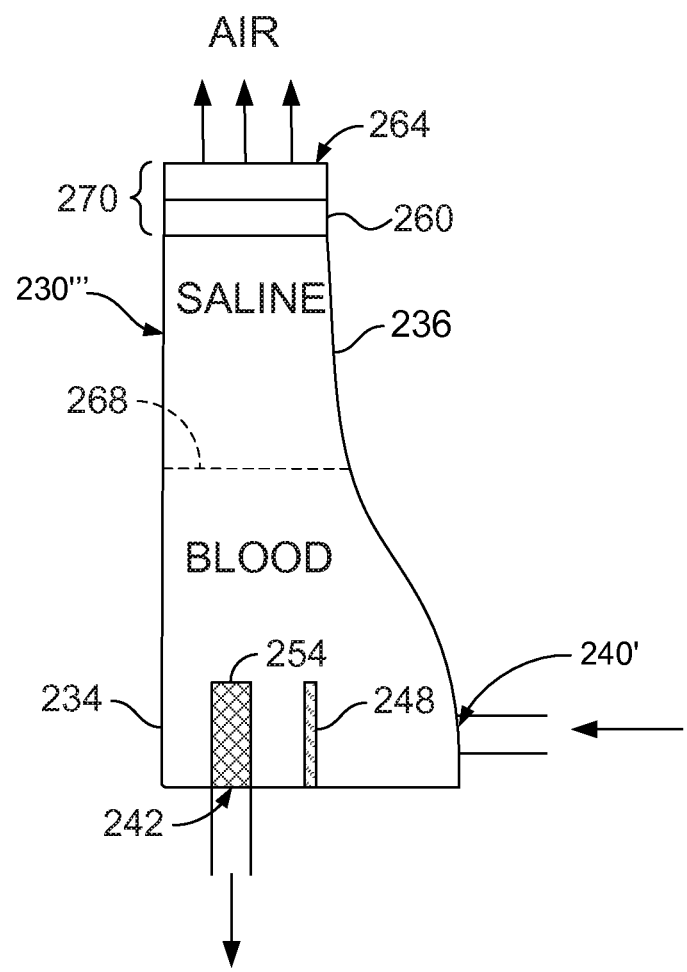

While air release chambers having entry and exit ports in a bottom region of the chamber have been described, in other implementations, as shown in FIG. 22C, at least one of the ports 240, 242 is located in a side surface of the chamber 230.

Figure 28:
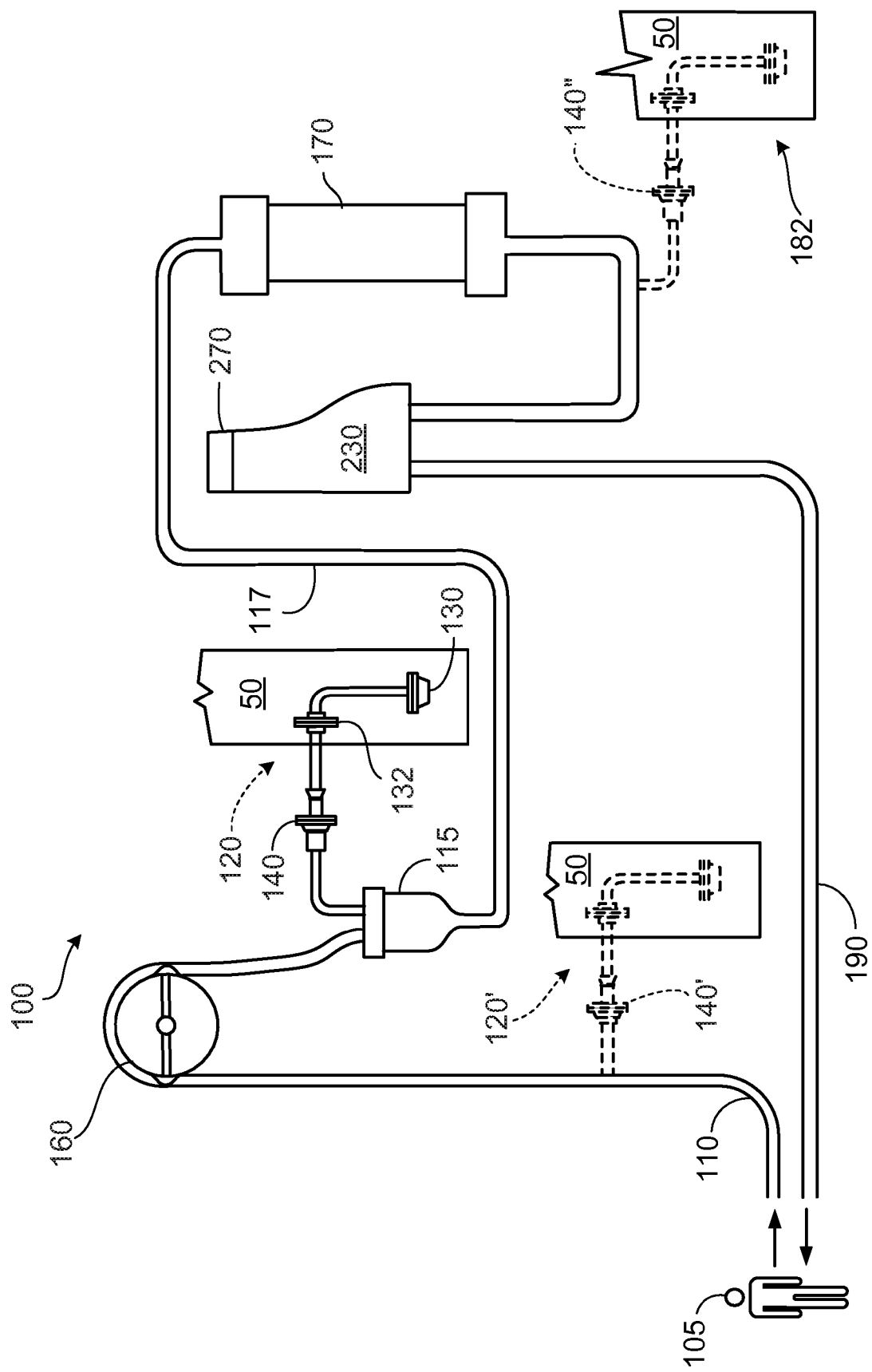
FIG. 28 is a schematic diagram of an extracorporeal circuit for a hemodialysis system including pre-pump and post-pump arterial pressure sensor assemblies and a venous pressure sensor assembly.

Although an embodiment of a extracorporeal circuit has been described in which an arterial pressure sensor assembly is arranged to measure a post-pump arterial pressure, in some embodiments, as illustrated in FIG. 28, an arterial pressure assembly 120' and associated external transducer protector 140' can, alternatively or additionally, be positioned upstream of the pump 160 for pre-pump arterial pressure measurement. In some embodiments, the circuit 100 can also include a venous pressure sensor assembly 182 and associated external transducer protector 140" in communication with the venous tubing 180, for monitoring the pressure of liquid (e.g., blood) flowing through the circuit 100 on the venous side. The venous pressure sensor assembly 182 can have the same construction as the arterial pressure sensor assembly 120 described above with regard to FIGS. 3A-5C. Furthermore, one or more electro-optical sensing assemblies, such as described above with regard to FIG. 19, can be provided for detecting color changes at any one or all of the external transducer protectors 140, 140', 140" disposed along the fluid circuit.

Figure 26:
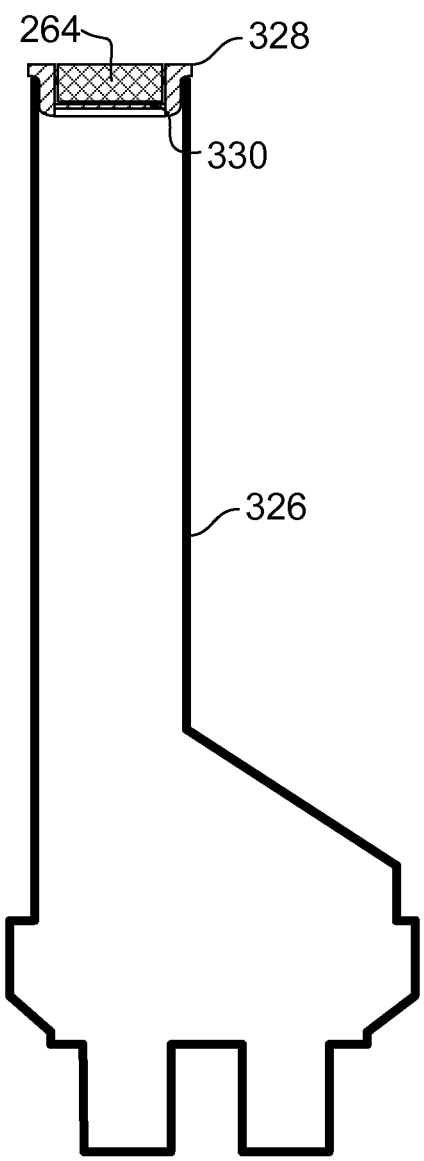
FIG. 26 is a schematic cross-sectional view of a bottom entry/bottom exit chamber and a vent assembly.
Figure 27:
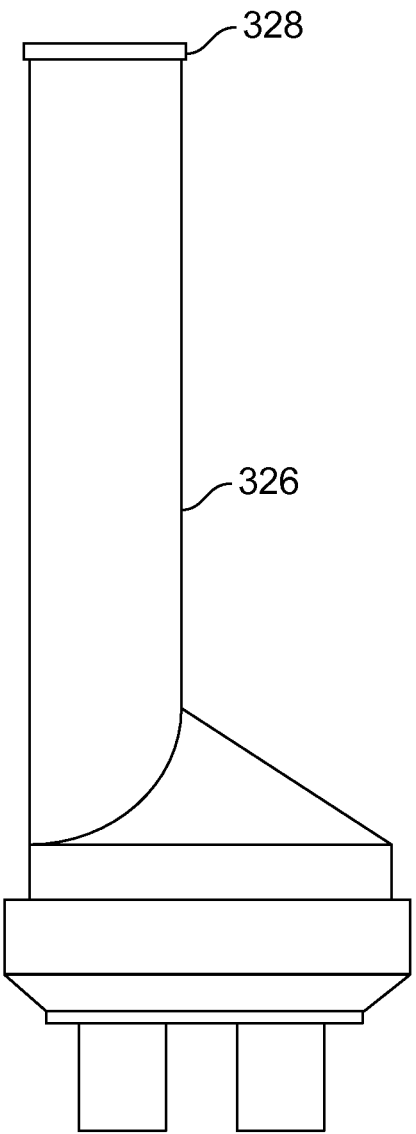
FIG. 27 is a schematic side view of a bottom entry/bottom exit chamber and a vent assembly.

Although certain implementations of a vent assembly have been described, in other implementations a different type of assembly can be formed. Referring to FIGS. 23, 23A and 23B, for example, a support 328 can have an inner diameter in which the micro-porous membrane 260 is held. The inner diameter of the support 328 can be x. The support 328 can have a flange that extends outwardly from the outer diameter at a top of the support 328. As shown in FIG. 24, the vent structure 264 can fit within the support 328 and on the micro-porous membrane 260. The micro-porous membrane 264 can be insert-molded into the support 328. The vent structure 264 can be press-fit into the support 328. Referring to FIGS. 25, 26 and 27, the support 328 is sized so that the support 328 fits into a chamber body 326 with the flange extending beyond the inner diameter of the chamber body 326 to inhibit (e.g., prevent) the support 328 from being pressed in or falling into the chamber body 326.

Although the vent assemblies described herein are shown as cylindrical, the assembly can have other shapes as well, such as rectangular, polygon, triangular or other suitable cross sectional shapes. Also, the vent assembly can have a threaded portion so that the assembly can be, for example, screwed into the air release chamber. Alternatively, the vent assembly can be welded, adhered with epoxy or otherwise fastened to the top of the chamber.

While air release chambers and transducer protectors have been described, the vent assemblies can be used in other extracorporeal fluid circuit components.

The components described herein can be used with other liquids, such as plasma, water, saline, and other medical fluids. Additionally, liquids other than saline can be used to prime the system. Other embodiments are within the scope of the following claims.

What is claimed is:

1. An extracorporeal medical fluid circuit component, comprising:
    a vent assembly comprising:
        a micro-porous membrane; and
        a vent structure adjacent to the micro-porous membrane, the vent structure comprising a porous material capable of changing color when the porous material is moistened, the porous material also being capable of swelling in a manner to create a seal that prevents the passage of liquid through the porous material when the porous material is moistened,
    wherein the component is capable of being used in an extracorporeal medical fluid circuit.

2. The component of claim 1, wherein the vent structure comprises a color change additive.

3. The component of claim 2, wherein the color change additive comprises powdered or granulated dye or a pH indicator.

4. The component of claim 2, wherein the color change additive comprises bromophenol blue.

5. The component of claim 1, wherein the vent structure comprises about 0.05% by weight to about 2% by weight of a color change additive.

6. The component of claim 1, wherein the vent structure includes polyethylene, polypropylene, or polystyrene.

7. The component of claim 1, wherein the vent structure comprises carboxymethylcellulose.

8. The component of claim 1, wherein the vent structure comprises a blend of polyethylene, carboxymethylcellulose, and a color change additive.

9. The component of claim 7, wherein a color change additive is covalently bonded to the carboxymethylcellulose.

10. The component of claim 1, wherein the vent structure comprises a blend of polyethylene, carboxymethylcellulose, and a pH indicator.

11. The component of claim 10, wherein the pH indicator is bromophenol blue.

12. The component of claim 7, wherein a pH indicator is covalently bonded to the carboxymethylcellulose.

13. The component of claim 1, wherein the vent structure has an average pore size of about 15 microns to about 45 microns.

14. The component of claim 1, wherein the vent structure has an average pore size of about 0.05 to about 0.45 microns.

15. The component of claim 1, wherein the micro-porous membrane has an average pore size of about 0.2 microns.

16. The component of claim 1, wherein the component is configured for use with a device adapted to remove air from blood.

17. The component of claim 1, wherein the component is capable of being used in a blood circuit.

18. The component of claim 1, wherein the micro-porous membrane is hydrophobic.

19. A system, comprising:
    a machine body;
    a pump on the machine body;

fluid circuitry in fluid communication with the pump, wherein the pump is configured to push fluid through the circuitry;

a vent assembly in fluid communication with the fluid circuitry, the vent assembly comprising:
a micro-porous membrane; and
a vent structure adjacent to the micro-porous membrane, the vent structure comprising a porous material capable of changing color when the porous material is moistened, the porous material also being capable of swelling in a manner to create a seal that prevents the passage of liquid through the porous material when the porous material is moistened.

20. The system of claim 19, wherein the system is a dialysis system.

21. The system of claim 20, wherein the dialysis system is a hemodialysis system.

22. The system of claim 19, further comprising an electro-optical assembly arranged to detect a change in color of the vent structure.

23. The system of claim 22, wherein the electro-optical assembly comprises
a light emitter arranged to emit light towards the vent structure; and
a light detector arranged to detect light reflected off of the vent structure.

24. The system of claim 23, further comprising a controller in electrical communication with the electro-optical assembly and the pump, wherein the controller is configured to halt operation of the pump in response to receiving a signal from the electro-optical assembly indicating that the vent structure has changed color.

25. The system of claim 23, further comprising a speaker; and a controller in electrical communication with the electro-optical assembly and the speaker,
wherein the controller is configured to sound an audible alarm through the speaker in response to receiving a signal from the electro-optical assembly indicating that the vent structure has changed color.

26. The system of claim 25, wherein the controller is configured to sound an alarm in response to receiving a signal from the electro-optical assembly indicating that the light detector detected reflected light having a wavelength that falls within a predetermined range.

27. The system of claim 26, wherein the predetermined range is 440 nm to about 490 nm.

28. The system of claim 23, further comprising a display; and a controller in electrical communication with the electro-optical assembly and the display,
wherein the controller is configured to provide a visual alarm on the display in response to receiving a signal from the electro-optical assembly indicating that the vent structure has changed color.

29. The system of claim 19, further comprising:
a pressure transducer; and
a transducer protector disposed between, and in fluid communication with, the fluid circuitry and the pressure transducer,
wherein the transducer protector comprises the vent assembly.

30. The system of claim 19, further comprising:
a chamber in fluid communication with the fluid circuitry, the chamber comprising
a fluid entry port; and
a fluid exit port,
wherein the fluid circuitry is configured to allow liquid to pass through the chamber from the entry port to the exit port, and
wherein the vent assembly is arranged to allow gas to exit the chamber through the vent assembly as the liquid passes through the chamber.

31. The system of claim 19, wherein the micro-porous filter is hydrophobic.

32. The component of claim 1, wherein the porous material of the vent structure is configured to allow gases to pass therethrough prior to being moistened.

33. The system of claim 19, wherein the porous material of the vent structure is configured to allow gases to pass therethrough prior to being moistened.

34. The component of claim 1, wherein the component is configured for use in a transducer protector.

35. A transducer protector comprising:
a body defining a fluid pathway; and
a vent assembly disposed within the fluid pathway, the vent assembly comprising
a micro-porous membrane; and
a vent structure adjacent to the micro-porous membrane, the vent structure comprising a porous material capable of changing color when the porous material is moistened, the porous material also being capable of swelling in a manner to create a seal that prevents the passage of liquid through the porous material when the porous material is moistened,
wherein the transducer protector is capable of being connected in fluid communication with a fluid circuit and a pressure transducer such that the vent assembly inhibits liquid flowing within the fluid circuit from contacting the pressure transducer.

36. The transducer protector of claim 35, wherein the porous material is capable of swelling when moistened.

37. The transducer protector of claim 35, wherein the micro-porous membrane is hydrophobic.

38. An extracorporeal medical fluid circuit apparatus, comprising:
a chamber including a fluid entry port and a fluid exit port; and
a vent assembly comprising:
a micro-porous membrane; and
a vent structure adjacent to the micro-porous membrane, the vent structure comprising a porous material capable of changing color when the porous material is moistened, the porous material also being capable of swelling in a manner to create a seal that prevents the passage of liquid through the porous material when the porous material is moistened,
wherein the fluid entry port and the fluid exit port are arranged to allow liquid to pass through the chamber from the fluid entry port to the fluid exit port, and
wherein the vent assembly is arranged to allow gas to exit the chamber as the liquid passes through the chamber.

39. The apparatus of claim 38, wherein the porous material includes an additive that is capable of swelling when moistened.

40. The apparatus of claim 38, wherein the micro-porous membrane is hydrophobic.

* * * * *

UNITED STATES PATENT AND TRADEMARK OFFICE
CERTIFICATE OF CORRECTION

PATENT NO.        : 8,663,463 B2                                     Page 1 of 1
APPLICATION NO.   : 12/388003
DATED             : March 4, 2014
INVENTOR(S)       : Weaver et al.

It is certified that error appears in the above-identified patent and that said Letters Patent is hereby corrected as shown below:

On the Title Page, Item [56]

On page 2, column 2 delete "Garnbro®" and insert --Gambro®--.

Signed and Sealed this
Twenty-seventh Day of May, 2014

Michelle K. Lee
*Deputy Director of the United States Patent and Trademark Office*